United States Patent
Tsushima et al.

(10) Patent No.: US 9,239,374 B2
(45) Date of Patent: Jan. 19, 2016

(54) BEAMFORMING METHOD, ULTRASONIC DIAGNOSTIC APPARATUS, PROGRAM, AND INTEGRATED CIRCUIT

(75) Inventors: Mineo Tsushima, Kyoto (JP); Yasuhito Watanabe, Osaka (JP); Takeo Kanamori, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 770 days.

(21) Appl. No.: 13/520,349

(22) PCT Filed: Nov. 9, 2011

(86) PCT No.: PCT/JP2011/006259
§ 371 (c)(1),
(2), (4) Date: Jul. 3, 2012

(87) PCT Pub. No.: WO2012/063481
PCT Pub. Date: May 18, 2012

(65) Prior Publication Data
US 2012/0281502 A1    Nov. 8, 2012

(30) Foreign Application Priority Data
Nov. 9, 2010    (JP) ................................. 2010-250449

(51) Int. Cl.
*G01S 7/52*    (2006.01)
*A61B 8/00*    (2006.01)
(Continued)

(52) U.S. Cl.
CPC ........... *G01S 7/52047* (2013.01); *A61B 8/4483* (2013.01); *G01S 7/52077* (2013.01);
(Continued)

(58) Field of Classification Search
CPC ............ G01S 7/52095; G01S 15/8927; G01S 7/52047; G01S 7/52077
See application file for complete search history.

(56) References Cited

U.S. PATENT DOCUMENTS

| 4,179,682 A | * | 12/1979 | Townsend | ...................... 367/135 |
| 4,180,792 A | * | 12/1979 | Lederman | ............. B06B 1/0622 |
| | | | | 342/380 |

(Continued)

FOREIGN PATENT DOCUMENTS

| CN | 1688897 A | 10/2005 |
| CN | 1856274 A | 11/2006 |

(Continued)

OTHER PUBLICATIONS

Chinese Office Action dated Jul. 24, 2014 issued in counterpart Chinese Application No. 201180005517.4.

(Continued)

*Primary Examiner* — Ari M Diacou
(74) *Attorney, Agent, or Firm* — Holtz, Holtz, Goodman & Chick PC

(57) ABSTRACT

A beamforming method according to the present invention is a method of processing echo signals of a target region which are obtained from a probe including a plurality of receiving elements arrayed on a predetermined line. The beamforming method includes the following steps (S1 to S3). At S1, seed beams are formed from echo signals received by at least two receiving elements from among the plurality of receiving elements. At S2, a main beam and sub beams are formed by synthesizing at least one of the seed beams. At S3, a narrow beam for the target region is formed by multiplying the sub beams by respective predetermined coefficients and subtracting the multiplied sub beams from the main beam. Here, an signal intensity for the target region regarding the main beam is higher than a signal intensity for the target region regarding each of the sub beams.

20 Claims, 21 Drawing Sheets

(51) Int. Cl.
*G01S 15/89* (2006.01)
*G10K 11/34* (2006.01)

(52) U.S. Cl.
CPC ......... *G01S 7/52095* (2013.01); *G01S 15/8927* (2013.01); *G10K 11/341* (2013.01); *G01S 15/8915* (2013.01)

(56) References Cited

U.S. PATENT DOCUMENTS

| | | | | |
|---|---|---|---|---|
| 4,228,686 | A * | 10/1980 | Tancrell | G01N 29/262 73/626 |
| 4,271,490 | A * | 6/1981 | Minohara | G01S 7/52047 367/122 |
| 5,186,177 | A * | 2/1993 | O'Donnell | A61B 8/12 600/447 |
| 5,278,757 | A | 1/1994 | Hoctor et al. | |
| 5,419,330 | A * | 5/1995 | Nishigaki | G01S 7/52046 600/447 |
| 5,617,862 | A * | 4/1997 | Cole et al. | 600/459 |
| 5,623,928 | A * | 4/1997 | Wright et al. | 600/447 |
| 5,879,303 | A * | 3/1999 | Averkiou | A61B 8/08 600/447 |
| 5,902,241 | A | 5/1999 | Seyed-Bolorforosh et al. | |
| 6,066,099 | A * | 5/2000 | Thomenius | G01S 7/52047 600/447 |
| 6,138,513 | A * | 10/2000 | Barabash | G01S 7/52047 367/105 |
| 6,179,780 | B1 * | 1/2001 | Hossack et al. | 600/437 |
| 6,224,556 | B1 | 5/2001 | Schwartz et al. | |
| 6,440,075 | B1 * | 8/2002 | Averkiou | G01S 7/52038 600/443 |
| 6,517,489 | B1 * | 2/2003 | Phillips et al. | 600/458 |
| 6,705,995 | B1 * | 3/2004 | Poland et al. | 600/447 |
| 8,045,777 | B2 | 10/2011 | Zwirn | |
| 2002/0143253 | A1 * | 10/2002 | Robinson | 600/437 |
| 2004/0122316 | A1 | 6/2004 | Satoh | |
| 2006/0173313 | A1 | 8/2006 | Liu et al. | |
| 2006/0253034 | A1 | 11/2006 | Fukukita | |
| 2008/0242992 | A1 | 10/2008 | Criton | |
| 2008/0262352 | A1 | 10/2008 | Zwirn | |
| 2009/0118616 | A1 * | 5/2009 | Liu et al. | 600/447 |
| 2009/0201206 | A1 * | 8/2009 | Li et al. | 342/373 |
| 2009/0306512 | A1 * | 12/2009 | Loftman et al. | 600/447 |
| 2010/0016725 | A1 * | 1/2010 | Thiele | 600/447 |
| 2010/0191115 | A1 * | 7/2010 | Denk | 600/447 |
| 2011/0098565 | A1 * | 4/2011 | Masuzawa | 600/443 |
| 2011/0307181 | A1 * | 12/2011 | Nagae | G01S 7/52047 702/19 |
| 2012/0213035 | A1 * | 8/2012 | Yoo et al. | 367/138 |
| 2012/0289835 | A1 * | 11/2012 | Hwang | G01S 7/52047 600/447 |
| 2014/0058262 | A1 * | 2/2014 | Yoda | A61B 8/44 600/443 |
| 2014/0078866 | A1 * | 3/2014 | Kanamori | A61B 8/4483 367/87 |

FOREIGN PATENT DOCUMENTS

| | | |
|---|---|---|
| JP | 10-127633 | 5/1998 |
| JP | 2002-272735 | 9/2002 |
| JP | 2003-325507 | 11/2003 |
| JP | 2006-204923 | 8/2006 |
| JP | 2006-217943 | 8/2006 |
| JP | 2008-526291 | 7/2008 |
| JP | 2010-158374 | 7/2010 |
| JP | 2010158473 A | 7/2010 |
| WO | 2006/070362 | 7/2006 |

OTHER PUBLICATIONS

International Search Report issued Dec. 20, 2011 in International (PCT) Application No. PCT/JP2011/006259.

Masayasu Ito et al., "Chiyouompa shindan souchi (ultrasonic diagnostic device)", Corona Publishing Co., Ltd., Aug. 26, 2002, p. 42-45, with partial English translation.

Extended European Search Report dated Jan. 9, 2015, issued in counterpart European Application No. 11840222.1.

\* cited by examiner

*PRIOR ART*

BEAMFORMING METHOD, ULTRASONIC DIAGNOSTIC APPARATUS, PROGRAM, AND INTEGRATED CIRCUIT

TECHNICAL FIELD

The present invention relates to ultrasonic diagnostic apparatuses, and more particularly at least to a beamforming method thereof.

BACKGROUND ART

Conventional ultrasonic diagnostic apparatuses generally employ a method called delay-and-sum method as a beamforming method for received ultrasound (for example, Non-Patent Literature 1).

FIG. 21 schematically shows the conventional delay-and-sum method.

A conventional ultrasonic diagnostic apparatus includes: a plurality of receiving elements 2101 that receive ultrasound; a plurality of delay units 2102 provided to the respective receiving elements 2101 to delay signals; and an addition unit 2103 that sums output signals of the delay units 2102.

In the delay-and-sum method, a signal received by each of the receiving elements 2102 is delayed for each element by the delay unit 2102 corresponding to the element. After delaying signals, the addition unit 2103 adds the delayed signals together to generate an addition result (signal 2103x) that is a sum of the signals.

CITATION LIST

Non Patent Literature

[NPL 1] "Chiyouompa shindan souchi (ultrasonic diagnostic device)", Masayasu Ito, Takashi Mochizuki, CORONA PUBLISHING CO., LTD.

SUMMARY OF INVENTION

Technical Problem

However, the beamforming using delay-and-sum method as employed in the conventional ultrasonic diagnostic apparatuses fails to form a beam, which is equivalent to a main-lobe of a received beam, steep (to have a high directionality) enough for a target region to be observed. As a result, resolution of image displaying ultrasonic receiving signals is not improved and the resolution is therefore lowered.

In addition, the conventional beamforming using delay-and-sum method has a further problem that noise signals from other regions except the target region are mixed to a beam indicating features of the target region, then S/N is lowered, and image quality of displayed image is deteriorated.

Thus, the present invention overcomes the problems of the conventional techniques as described above. One non-limiting and exemplary embodiment provides a beamforming method, a ultrasonic diagnostic apparatus, and the like, which are enable to provide high quality of received images with more suppressed noises and higher resolution of ultrasonic diagnostic images.

Solution to Problem

In one general aspect, the techniques disclosed here feature; a beamforming method of processing echo signals of a target region, the echo signals being obtained from a probe including a plurality of receiving elements arrayed on a predetermined line, the beamforming method including: forming seed beams from echo signals received by at least two receiving elements from among the plurality of receiving elements; forming a main beam and sub beams by synthesizing at least one of the seed beams; and forming a narrow beam for the target region, by multiplying the sub beams by respective predetermined coefficients and subtracting the multiplied sub beams from the main beam, wherein a signal intensity for the target region regarding the main beam is higher than a signal intensity for the target region regarding each of the sub beams.

It should be noted that the above-mentioned narrow beam refers to a beam having a main-lobe with a width narrow enough for appropriate operations (see a range 81 $m$ in FIG. 4B and a range 82 $m$ in 5B).

Advantageous Effects of Invention

With the above structure, a beam narrower than the conventional beams can be implemented. As a result, when signals for which beamfroming is performed by the beamforming method according to the present invention, it is possible to increase resolution and image quality.

DESCRIPTION OF EMBODIMENTS

The following describes embodiments according to the present invention with reference to the drawings.

Figure 4:
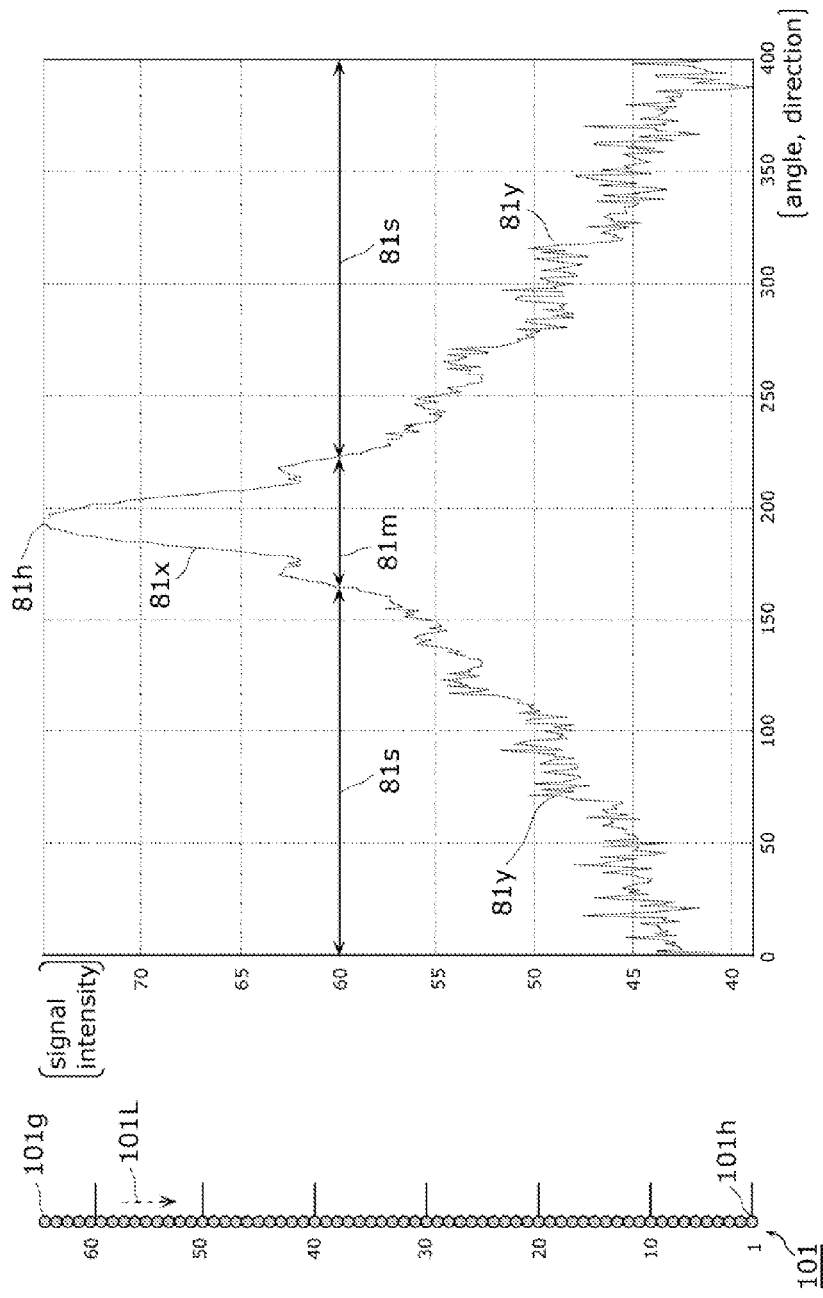
FIG. 4A is a diagram showing receiving elements in the case where all of the receiving elements are used.
FIG. 4B is a graph plotting beam features in the case where a seed beam is to be formed by using signals generated by all receiving elements.
Figure 5:
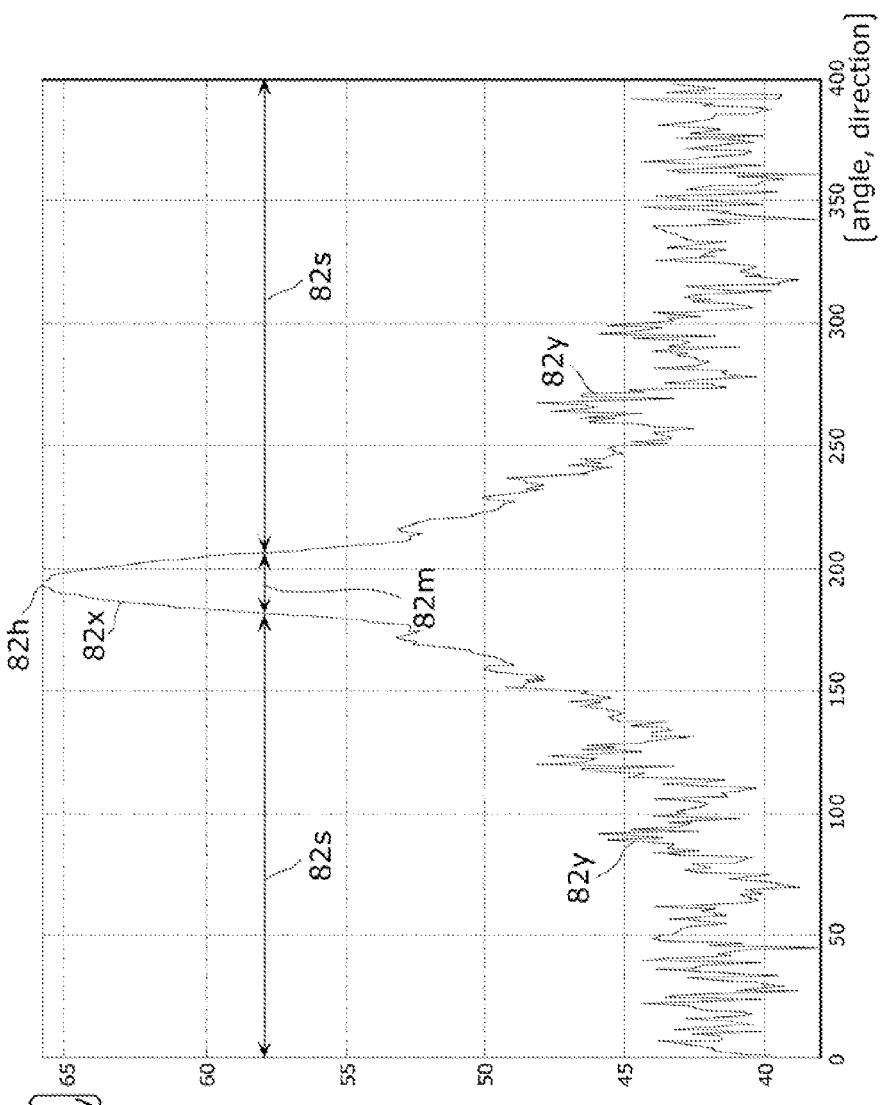
FIG. 5A is diagram showing receiving elements in the case where a part of all receiving elements are used.
FIG. 5B is a graph plotting beam features in the case where a seed beam is to be formed by using signals generated by a part of the receiving elements.

The beamforming method according to the embodiments is a beamforming method of processing echo signals (a plurality of signals 205a in FIG. 25) of a target region (see an observation point 101s in FIG. 1) which are obtained from a probe unit 101 including a plurality of receiving elements 109 (FIG. 25) arranged along a predetermined line (see a straight line 101L in FIG. 4A). The beamforming method includes the following steps. First, at a seed beam forming step, a seed beam group forming unit 202M forms a plurality of seed beams (signals 202b) by using the echo signals obtained from at least two receiving elements 109 among the receiving elements 109. Then, at a beam synthesis step, a main beam (main signal 92) and a plurality of sub beams (a plurality of sub signals) are formed from one or more seed beams by using the seed beams among the formed seed beams. At a narrow beam forming step, a narrow beam (signal 105a) of the target region is formed. The narrow beam has an intensity that is obtained by subtracting a predetermined first intensity from an intensity of the main beam. (The first intensity is an intensity that is obtained by adding (summing) intensities, each of which is calculated by multiplying an intensity of each of the sub beams by a predetermined coefficient corresponding to the sub beam.) Here, an intensity (relative intensity) relative to a predetermined second intensity (as described later) of a signal (see a signal 82x) in a range (see a range 82m) corresponding to the target region regarding the main beam (see FIG. 5B) is greater than an intensity (relative intensity) relative to the above-mentioned second intensity of a signal (see a signal 81x) in a range (range 81m) corresponding to the target region in any one of the sub beams (see FIG. 4B). It should be noted that, for example, the above-described relative intensity is an intensity relative to the intensity (the above-described second intensity) of the signal (signal 81y, signal 82y) in the other ranges (range 82s, range 81s) except the above-described range (see range 82m, 81m) corresponding to the target region. It is also possible, for example, that the main beam (FIG. 5B) has the relatively narrow range (range 82m) corresponding to the target region and has the relatively great relative intensity, and in contrast that each of the sub beams (FIG. 4B) has the relatively wide range (range 81m) corresponding to the target region and has the relatively small relative intensity.

As described above, for example, the following processing may be performed.

It is possible that the intensity of the beam (signal 105a) to be formed is obtained by subtracting the intensity of the sub signal 91 from the intensity of the main signal 92.

Here, the sub signal 91 is, for example, the above-described signal having the first intensity that is the summed intensity.

It is also possible that each of the main signal 92 and the sub signal 91 is formed.

An intensity of each of the formed signals may be a sum of a plurality of intensities.

Each of intensities to be summed may be an intensity that is obtained by multiplying an intensity of each of the echo signals 205a, which corresponds to the intensity among the echo signals 205 provided from the probe 101, by a coefficient.

The coefficient to be multiplied may be a coefficient corresponding to (a) the echo signal 205a having an intensity to be multiplied by the coefficient and (b) the above-described signal to be generated to have an intensity generated by summing multiplied intensities, from among a plurality of coefficients included in a coefficient group.

The above-described coefficient group to be used may be a relatively appropriate coefficient group which is determined from a plurality of coefficient groups by experiments or the like.

The relatively appropriate coefficient group is, for example, a coefficient group or the like which is used to form a relatively appropriate beam (signal 105a).

The relatively appropriate beam is, for example, a beam having a main lobe (see range 82M in FIG. 5B) with a relatively narrow width and having a main lobe signal (see signal 82x) with a relatively steep inclination.

Thereby, the resulting formed beam (signal 105a) is more appropriate.

Therefore, image quality of an image 106a (FIG. 1) generated from the formed beam (signal 105a) can be increased to have, for example, a relatively high resolution.

It is also possible that, in forming respective seed beams, when at least two of the above-described receiving elements are combined, a combination for a seed beam and another combination for another seed beam are different, so that the seed beam is formed by using an echo signal generated by each receiving element in the seed beam combination.

This is described in more detail below.

Figure 1:
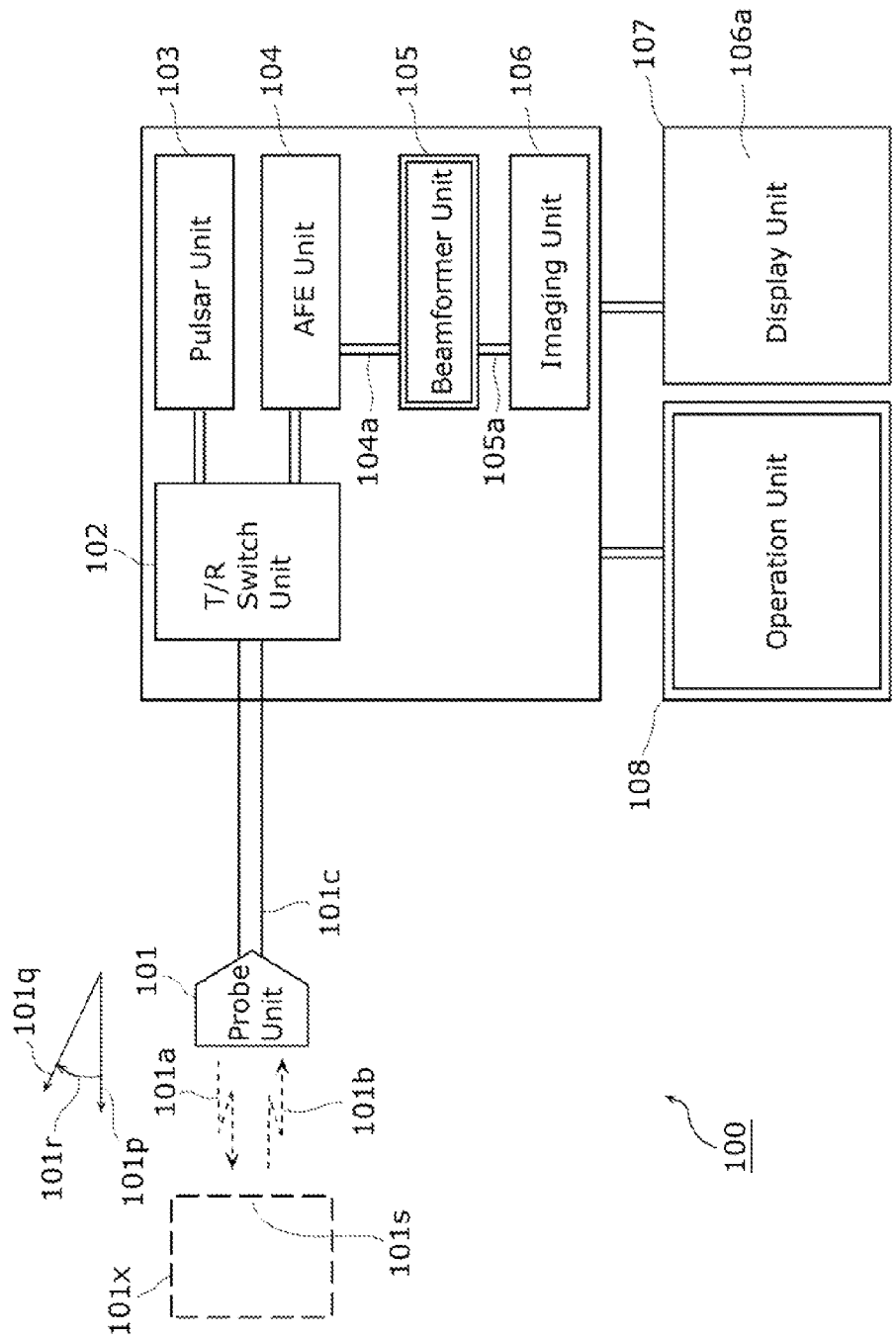
FIG. 1 is a diagram showing a structure of an ultrasonic diagnostic apparatus.

FIG. 1 shows a structure of an ultrasonic diagnostic apparatus (apparatus 100).

The ultrasonic diagnostic apparatus includes a probe unit 101, a T/R switch unit 102, a pulsar unit 103, an AFE unit 104, a beamformer unit 105, an imaging unit 106, a display unit 107, an operation unit 108, and the like.

The probe unit 101 transmits ultrasound (ultrasound 101a) towards a body and receives reflection waves (reflection waves 101b) of the transmitted ultrasound.

The T/R switch unit 102 electrically switches between a transmission signal and a received signal in terms of circuit protection and the like.

The pulsar unit 103 generates electrical signals to facilitate ultrasound transmission.

The AFE unit 104 receives reflection waves of the ultrasound reflected on a body or the like, then performs signal amplification and the like on the received reflection waves, and converts the amplified reflection waves from analog to a digital signal sequence (signal sequence 104a).

The beamformer unit 105 performs so-called beamforming on the received signal sequence by array signal processing. The beamforming is equivalent to focus processing on a region to be visible.

The imaging unit 106 generates a display image from the signal (signal 105a) generated by the beamforming unit.

The display unit 107 displays the output (image 106a) of the imaging unit 106.

Furthermore, the ultrasonic diagnostic apparatus includes the operation unit 108 and the like by which a user of this ultrasonic diagnostic apparatus such as a physician performs operations to control a series of processes.

The technique of the embodiments is characterized especially by the beamformer unit 105 that performs arithmetic operations on received signal (signal sequence 104a) of ultrasound to form a beam (signal 105a) to generate a diagnostic image. Therefore, the following especially describes the beamformer unit 105 and explains a structure, functions, and the like of the beamformer unit 105 in more detail.

It should be noted that units except the beamformer unit 105 that is the characteristic part of the present invention are not described in detail. For example, a structure of an apparatus to which the technique of the present invention is applied may be a structure of a conventional ultrasonic diagnostic apparatus. For example, for a structure of a beamformer unit in the conventional ultrasonic diagnostic apparatus, the structure of the beamformer unit (beamformer unit 105) of the present invention may be introduced to implement a ultrasonic diagnostic apparatus to which the technique of the present invention is applied.

It should also be noted that the ultrasonic diagnostic apparatus according to the present invention is not limited to the ultrasonic diagnostic apparatus having the structure shown in FIG. 1. For example, if a transmission element is different from a receiving element, the T/R switch unit 101 can be eliminated. It should also be noted that in the structure of the appliance according to the present invention, the pulsar unit 103 and/or the AFE unit 104 may be embedded in the probe unit 101.

The following describes Embodiment 1 regarding the beamforming unit in the ultrasonic diagnostic apparatus according to the present invention.

Embodiment 1

Figure 2:
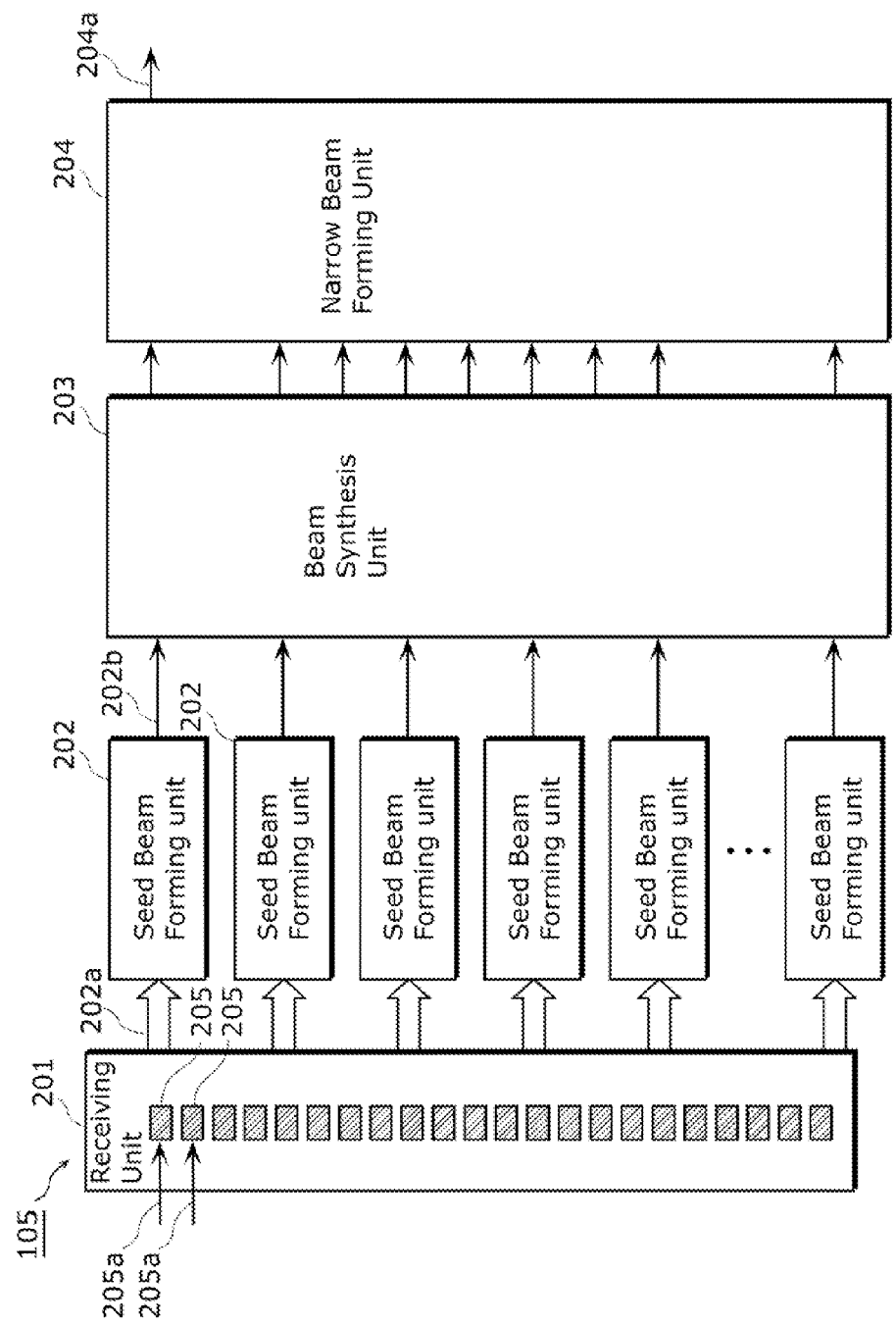
FIG. 2 is a block diagram showing a receiving method of the ultrasonic diagnostic apparatus.

FIG. 2 is a diagram showing a structure of the beamformer unit (the beamformer unit 105 in FIG. 1) according to Embodiment 1.

The beamformer unit includes a receiving unit 201, a plurality of seed beam forming units 202, a beam synthesis unit 203, and a narrow beam forming unit 204.

The receiving unit 201 includes a plurality of receiving elements 205.

Each of the receiving elements 205 receives the following signal.

Each of the receiving elements 205 receives a signal (signal 205a) which is generated by receiving a signal (signal 101c in FIG. 1) of reflection waves 101b which are received by the probe and performing amplification, processing such as A/D conversion to digital signal, and the like on the received signal.

Furthermore, the beamformer unit includes the plurality of seed beam forming units 202.

Each of the seed beam forming units 202 forms a beam (seed beam) from received signal sequences which are received from respective receiving elements 205 included in a combination corresponding to the seed beam forming unit 202.

Here, for each of the seed beam forming units 202, a beam formed by using received signal sequences which are received from respective receiving elements 205 included in a predetermined combination (combination corresponding to the seed beam forming unit 202) is in referred to as a "seed beam" in the present invention.

In other words, each of the seed beam forming units 202 forms a seed beam by using a combination corresponding to the seed beam forming unit 202 from among pre-set combinations (available combinations of elements to be used) for a plurality of received signal sequences generated by the above-described receiving units 201, thereby performing beamforming of the seed beam.

Therefore, a plurality of beams (beam 202b) generated from different combinations of used elements are formed.

Moreover, the beamformer unit includes the beam synthesis unit 203 that receives the plurality of beams (seed beams) from the seed beam forming units 202 and performs beam synthesis.

Furthermore, the beamformer unit includes the narrow beam forming unit 204 that uses a plurality of synthesized beams formed by the beam synthesis unit 203 and, if needed, a plurality of seed beams received from the seed beam forming units 202 as input values, and thereby forms a barrow beam (barrow beam 204a) for a predetermined display area.

The seed beam forming units 202 use received signals of all of the receiving elements, or intentionally use only received signals of a part of the receiving elements instead of received signals of all of the receiving elements. It is thereby possible to increase a directivity of a received beam with respect to a specific direction in comparison to the case where all of the receiving elements are used, so that the beam has a sharper directivity.

The plurality of seed beam forming units 202 form a plurality of seed beams by using two or more kinds of combinations of used receiving elements, in order to form a plurality of seed beams having different directivities (various kinds of seed beams).

The beam synthesis unit 203 performs arithmetic operations such as addition, multiplication, and subtraction on the seed beams to increase variations (kinds) of the seed beams. The addition, the processing of subtraction, multiplication, and the like on the plurality of the seed beams is referred to as "beam synthesis" in the present invention.

Next, from the resulting various beams, the beam synthesis unit 203 forms (a) a narrow-directional beam (hereinafter, referred to as a "main beam" in the present invention) that has a high signal intensity indicating a region including a target region, and (b) beams (hereinafter, referred to as "sub beams" or "null beams" in the present invention) each of which has a low signal intensity for the target region in order to cancel noise caused by regions except the target region.

Next, the narrow beam forming unit 204 subtracts the sub beams from the main beam formed by the beam synthesis unit 203, so as to form a beam having a stronger directivity to the target region in comparison to non-target regions.

With the above structure, it is possible to form a beam having a narrow directivity for the target region in comparison to the conventional beamforming method in which delay-and-sum method is performed on signals obtained by using all receiving elements. As a result, noise caused by regions except the target region is suppressed, and the steep beam is able to have signal characteristics having high resolution.

The following describes each of units included in the unit for generating received signals, namely, the beamformer unit in more detail. It should be noted that the structure of each unit is not limited to the complete structure described below, but of course, appropriate simplification or the like of the structure is possible depending on a use or design of the apparatus.

<Receiving Unit>

A transmission unit that transmits ultrasound signals transmits ultrasound signals. Although not shown, after the transmission, the ultrasound signals transmitted towards a body is reflected on a position of a variance or the like of a medium of the body. The resulting reflection waves are received by the receiving unit 201.

Here, the number of the receiving elements in the receiving unit 201 may be one, but it is assumed in the present embodiment that the receiving unit 201 includes a plurality of receiving elements (receiving elements 205).

The receiving unit 201 generally performs a series of processes called an "analog front end processing".

The analog front end processing means a series of processes performed by the receiving elements to amplify the ultrasound signals received by the receiving elements and convert the resulting signals to digital signals using an A/D converter or the like.

Therefore, the output signals of the receiving unit 201 are digital signal sequence which is generated by being received, amplified, and A/D converted by respective receiving elements.

Although various transmission waves of ultrasound have been proposed, general pulse waves are assumed in the description without limiting to specific waves.

A plurality of digital signal sequences (pieces of data 202a) are provided from the receiving unit 201 to the respective seed beam forming units 202.

The input data 202a includes signals obtained from corresponding receiving elements 205 in the receiving unit 201.

It should be noted that it has been described that each of the receiving elements in the receiving unit 201 receives ultrasound, but the structure is not limited to the above. For example, an ultrasound probe (not shown) not the receiving unit 201 may receive ultrasound. Then, the receiving unit 201 may perform amplification and A/D conversion on signal obtained by each of the receiving elements included in the receiving unit 201 by using the receiving element, and the ultrasound may be received by the outside of the receiving unit 201. It should be noted that the receiving unit 201 may be included in the AFE unit 104 equivalent to the analog font end as described above, not in the beamforming unit 202.

<Seed Beam Forming Unit>

A structure and operations of the seed beam forming unit 202 are described with reference to FIG. 3.

Figure 3:
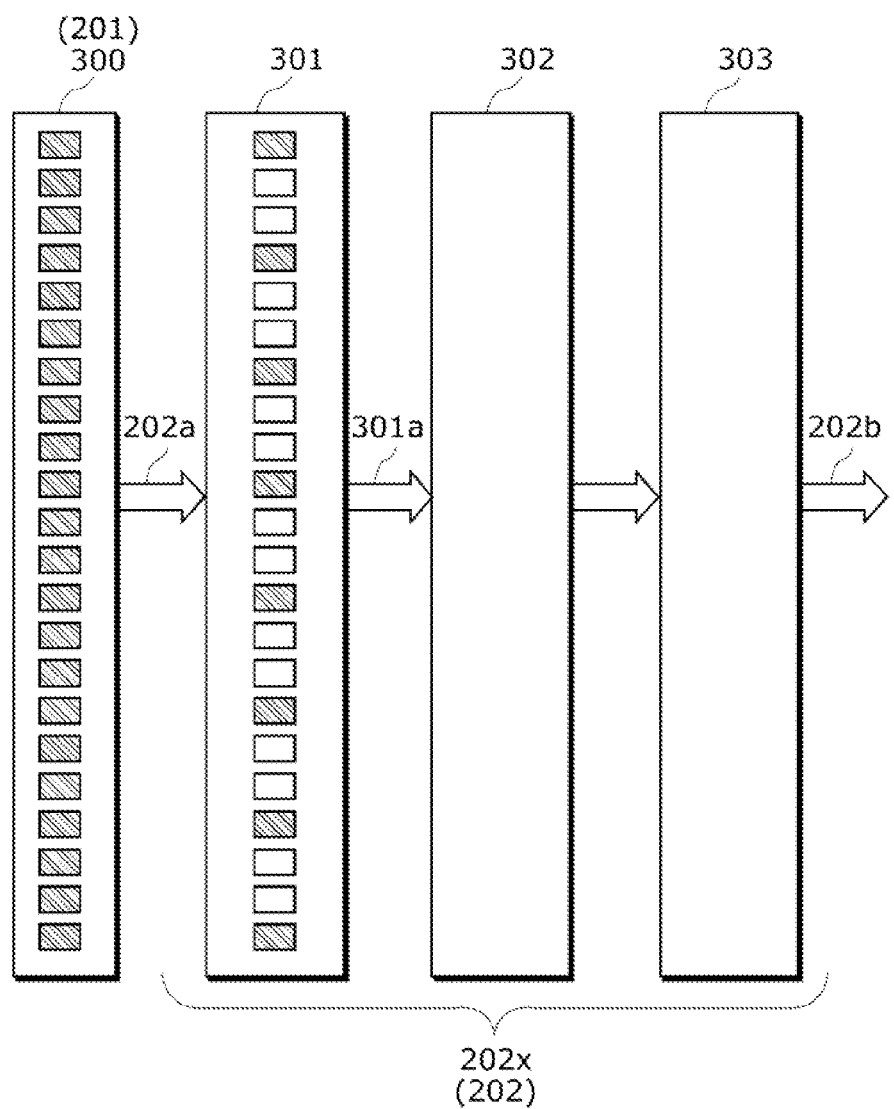
FIG. 3 is a block diagram showing a seed beam forming unit.

FIG. 3 is a block diagram showing the seed beam forming unit 202x.

The seed beam forming unit 202x in FIG. 3 is one of the seed beam forming units 202 shown in FIG. 2.

As described in more detail below, for example, each of the seed beam forming units 202 except the seed beam forming units 202x in FIG. 3 as among the seed beam forming units 202 shown in FIG. 2 have the same structure and operations as those of the seed beam forming unit 202 in FIG. 3.

The receiving unit 300 corresponds to the receiving unit 201 (or signal inputted to the beamformer unit 105) shown in FIG. 2. Each part (each square) in the receiving unit 300 shows each receiving element (or signal itself received by each receiving element).

The seed beam forming unit 202x includes a seed beam switch unit 301, a preparation unit 302, and a delay addition processing unit 303.

The seed beam switch unit 301 is a switch for using only received signal sequences in a predetermined element combination from among received digital signal sequences (pieces of data 202a in FIG. 2) corresponding to the respective receiving elements which are obtained from the receiving unit 300 (or from the outside of the beamformer unit).

In other words, for example, the data 301a outputted by the seed beam switch unit 301 includes one or more signals (signal sequences). The one or more signals include only a signal (signal sequence) provided from the receiving element 205 included in the above-described combination in the seed beam forming unit 202x, from among signals (signal sequence) which are included in the pieces of input data 202a and provided from the receiving elements 205. In other words, the one or more signals do not include signals (signal sequence) provided from receiving elements 205 which are not included in the combination.

It should be noted that the seed beam switch 301 performs the above-described processing by switching connection to each of the receiving elements 205 (FIG. 2). Moreover, the seed beam switch 301 may, for example, selectively extract received signal to be used, without switching connection to each of the receiving elements. The seed beam forming unit 202x may selectively extract received signals to be used, under the control of the control unit, without including the seed beam switch 301.

For example, in FIG. 3, a receiving element selected by the seed beam switch unit 301 from among the received digital signal sequences indicated by the seed beam switch unit 301, namely, only a received digital signal sequence of an element corresponding to the receiving element to be used to form a seed beam is shown as hatched. Here, a total number of receiving elements is assumed to be 22.

Of course, the total number of the receiving elements has been described as 22 only as an example. The total number is not limited to 22, but generally is 32, 48, 64, or the like.

As described, the number of signals included in the input data 202a may be 22 that is the same as the number (22) of the squares (receiving elements) included in the receiving unit 300 in FIG. 3.

The number of the signals included in output data 301a may be 8 that is the same as the number (8) of the hatched squares included in the seed beam switch unit 301 in FIG. 3.

It should be noted that it has been described in the present embodiment that the ultrasound receiving elements in the probe 101 and the receiving elements (signal sequences) have a one-to-one relationship as an example. However, one receiving element may not receive signals of ultrasound receiving elements near the receiving element.

The seed beam switch unit 301 (or the control unit) selects a part of received signal sequences (a part of the receiving elements 205) from among all of the received signal sequences, and forms a seed beam from the selected part of the received signal sequences (signals from respective selected receiving elements 205).

It is desirable that there is at least one receiving element, which is not used to form a seed beam, between two of the selected receiving elements.

In the case where received signals of all of the receiving elements are used in the same manner as the conventional beamforming method, and in the case where only a part of the signals of the receiving elements is used in the manner as described in the present embodiment, the following occurs when delay-and-sum method is in performed on a receiving element (received signal) to be used. The case of the present embodiment where only a part of the signals is used can provide steeper main lobe and narrower directivity of beam characteristics (see FIGS. 4 and 5 as described later).

The following compares an example of a seed beam formed by the conventional method to an example of a seed beam formed in the present embodiment.

FIGS. 4A and 4B show signal characteristics in the case where signals of all of the receiving elements are used in the manner as the conventional beamforming method.

FIG. 4A shows a case where the receiving unit includes 64 receiving elements and forms beams by using signals of all of the 64 receiving elements (the above-described case using the conventional method).

FIG. 4B is a diagram showing beam characteristics formed by the signals in the case where all of the receiving elements are used as in FIG. 4A.

A horizontal axis in FIG. 4B indicates a position in a direction of arranging the receiving elements (vertical direction in FIG. 4A), and a vertical axis in FIG. 4B indicates a signal intensity of a beam.

As shown in FIG. 4B, a main lobe appears at a center position, while smooth attenuation is seen at both sides of the main lobe. As the side lobe is more away from the center position, stronger suppression is applied.

FIGS. 5A and 5B show an example of a seed beam formed by the beamforming method according to the present embodiment.

FIG. 5A shows receiving elements to be used and receiving elements not to be used.

FIG. 5B shows a shape of a formed beam.

Vertical and horizontal axises in FIG. 5B are the same as the vertical and horizontal axises in FIG. 4B, respectively.

FIG. 5A shows an example where every third receiving element is set to be used.

In other words, there are two receiving elements not to be used between two receiving elements to be used in beam forming.

Here, the receiving elements to be used are shown as shadowed.

As shown in FIG. 5A, when a part of received signals is selected from the receiving elements (received signals) and then a seed beam is formed, it is seen that as shown in FIG. 5B, a width of the main lobe is narrower than that in the conventional example.

On the other hand, it is also seen that a signal of the side lobe is stronger than that in the conventional example.

As described above, if a seed beam is formed by selecting a part of the receiving elements (received signals), it is possible to provide a beam having a higher directivity than the conventional one.

On the other hand, it is considered that a signal of the side lobe is stronger than that in the conventional example. The problem may be solved by, for example, a beam synthesis unit or the like that is described later.

Although a pattern of the selected received signals has various examples, it is characterized by forming a signal having a higher directivity (a signal width of a main lobe is narrow, and instead, in comparison to the case where all the elements are selected, a level of in a side lobe is increased) in comparison to a beam profile in the case where all of the received signals are summed in the same manner as the conventional beamforming method.

Furthermore, the beam synthesis unit or the like that will be described later may select, as a beam directivity pattern, a combination to be used based on a pattern (combination) to be selected by a desire to have a plurality of beam directivity patterns as beam directivity patterns in the beam synthesis unit or the like that is described later, or based on a combination capable of forming a formed signal to have an acoustic blind angle for a target region, which is called a null beam.

A signal having a high directivity means a signal having a main lobe with a narrow horizontal width. For example, a seed beam formed by the present embodiment has a main lobe with an intensity range lower than a peak intensity of the main lobe by 10 dB to 15 dB and with a horizontal width equivalent to an intensity range of 70% to 80% of the peak intensity, and each of the intensity range and the horizontal width is narrower than that in the conventional example.

The combination pattern of received signals is arbitral in comparison to the conventional generated signals as described above, if the combination patter is predetermined to generate signals having a high directivity. For example, the following combination examples (combination pattern 1, combination pattern 2, and combination pattern 3) can be considered.

Figure 6:
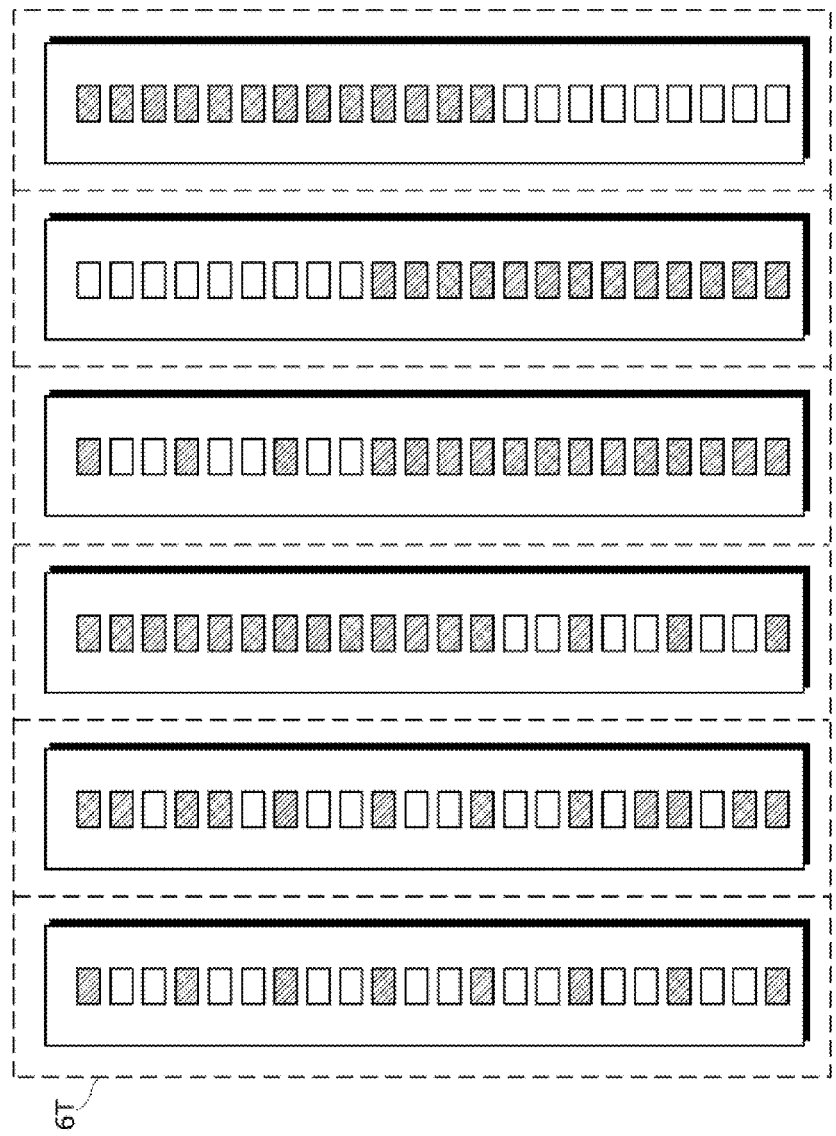
FIG. 6 is a diagram showing an example of selection of the receiving elements by a seed beam switch.

FIG. 6 is a diagram showing a pattern of a combination of receiving elements to be used.

(1) Pattern 1

The seed beam switch 301 in FIG. 3 shows an example of the combination pattern.

FIG. 3 shows a pattern in the case where received signals of the receiving elements to be selected are regularly selected.

Pattern 1 is the pattern shown in FIG. 3. As shown in the left-most column (the first column in Table 6T) in FIG. 6, receiving elements to be selected are evenly arranged in this combination pattern.

More specifically, the number of non-selected receiving elements located between selected two receiving elements is the same because each group of two receiving elements contains the same-numbered receiving elements (2 in the example of FIG. 6).

In other words, there is the following case of two selected receiving elements (for example, two receiving elements which are the fourth and seventh from the top in the first column). There are only non-selected receiving elements (the fifth and the sixth) between these two receiving elements, and no selected receiving element. Regarding such a group of two receiving elements (for example, a group of the fourth and the seventh, a group of the seventh and the tenth), each group contains the same-numbered (2 in the example of the first column in Table 6T) non-selected receiving elements (the fifth and the sixth, the eighth and the ninth) between two receiving elements in the group, as described above.

Here, the number of continuous receiving elements having signals to be used (1 in the example of the first column in Table 6T) may be any number, as long as the obtained signal has a directivity higher than that of a beam formed by using all of the receiving elements.

(2) Pattern 2

Pattern 2 (the second column in Table 6T) of a receiving element combination is a pattern in which positions of respective receiving elements to be used are symmetrical to the center of a receiving opening (a part between the eleventh and twelfth receiving elements), and a receiving element (the 22nd, 21st, 20th, . . . ) that is symmetrical to the above center part for any one of the receiving elements to be used (the first, second, fourth, . . . ) is also used.

More specifically, if each of receiving elements to be used is divided into a part above the center part and a part below the center part (both edge parts), the same selection patters (symmetrical two patterns) are arranged above and below the center part. In other words, the pattern above the center part is symmetrical for the pattern below the center part.

The Pattern 2 relatively averages sonic unevenness and influence of various noises in a body. Therefore, it is relatively easy to stabilize beam directivity.

Furthermore, as seen in FIG. 5A as previously described, if the center part 101y (a part between the eleventh and the twelfth in the example of the second column in FIG. 6 as described previously) of each of the elements (opening end elements) at both ends of each of the receiving elements to be used is positioned at a boundary (part between two receiving elements) between the receiving element and a receiving element adjacent to the receiving element, receiving elements to be used are selected so that receiving elements are symmetrical between above and below to a boundary line of the boundary. It should be noted that it is not necessary to always use the receiving elements when the receiving element is positioned at the center part 101y, and such a receiving element may not be used. In short, any pattern is possible as long as the pattern is symmetrical to a horizontal line (or) a vertical line).

Like Pattern 2, if a combination of receiving elements to be used is symmetric to a horizontal line, it is possible to improve a directivity of formed seed beam.

(3) Pattern 3

In Pattern 3 (the third column in Table 6T in FIG. 6), receiving elements (the first and 22nd receiving elements in Table 6T) at the top and the bottom (both edge parts) are selected from among the receiving elements. The selection pattern indicated by the seed beam switch 301 in FIG. 3 is an example.

In general, as an interval (opening) between two receiving elements is increased to, for example, a maximum, a main lobe of a received beam is generally steeper.

Therefore, when influence to a side lobe or a magnitude of received energy are ignored, it is possible to obtain a beam having a steeper main lobe and narrower directivity when an interval between the two receiving elements is increased as much as possible in forming a received beam.

Here, one or more received signals (one or more receiving elements) selected by the seed beam switch unit 301 are desirably at least two received signals (receiving elements).

More specifically, if the number of selected receiving elements is relatively large, total energy of input beam is increased. Therefore, it is possible to largely obtain an energy difference between a part with an intensity of received signals (an intensity equal to or higher than a threshold value) and a part without intensity. Therefore, as the number of selected receiving element is larger, it is generally possible to improve S/N or contrast in image display.

It should be noted that a combination of receiving elements (received signals) selected by the above-described seed beam switch 301 is not limited to any one of the above-described patterns 1 to 3. Any combination of selected receiving elements is possible as long as a beam width of a main lobe of an obtained seed beam is narrower than a beam width of a seed beam formed by using all of the receiving elements and a signal having a higher directivity can be obtained.

It is also possible to combine the above-described examples to increase the number of openings (see the above-described Pattern 3) for a target region, to regularize (see Pattern 1), and to reduce receiving elements to be symmetrical to a horizontal line (see Pattern 2), thereby generating a signal having a steep main lobe.

Here, the beam width is referred to as a width in a range of a direction (see a horizontal axis in FIGS. 4B and 5B, and the like) with respect to an intensity that is lower than a peak intensity of a main lobe by 15 dB.

The description is back to the seed beam forming unit 202x with reference to FIG. 3.

There are at least two combinations of signal sequences to be used, which have been described for the received signal sequences selected by the seed beam switch unit 301.

For example, between two seed beams which are a beam formed by the top seed beam forming unit 202 at the top and a beam formed by the second seed beam forming unit 202 from the top, the (above-described) combination of input digital signal sequences (receiving elements) to be used is different.

As described above, in at least a part of the seed beams formed by the plurality of seed beam forming units 202, each of the beams are formed by selectively using signal obtained from a part of the receiving elements and therefore has a relatively high directivity.

It is desirable that there is at least one receiving element (received signal) not to be used, between two receiving elements (received signals) to be used. There are at least two kinds of combinations of receiving elements to be used, so that plural kinds of seed beams having different signal characteristics are formed.

The above-described examples have been given for a method of forming a seed beam having a relatively high directivity so that a seed beam having a main lobe with a steep width can be synthesized.

On the other hand, in order to cancel noise occurred in regions except the target region, only a certain number of seed beams (about 5 or 6 seed beams) are formed to eventually synthesize a beam which is for the target region and has a directivity with a relatively low intensity.

By forming seed beams having a low directivity, it is possible to cancel more noise in regions except the target region and to improve S/N ratio. It should be noted that whether or not to form seed beams having a low directivity depends on a beam pattern of the beam to be formed, a position of the target region, or the like, and is arbitral.

The pattern shown at the rightmost side (the sixth column in Table 6T in FIG. 6) and the second pattern from the rightmost side (the fifth column) have less openings (13 for each of the sixth and fifth columns) and therefore have a lower beam directivity. Then, as described later, if necessary for forming a main beam and sub beams, the seed beam forming unit 202 that operates with such patterns may be included in the apparatus 100 as one of the seed beam forming units 202.

It should be noted that the pattern shown in the fourth column in table 6T is not described in detail.

The received digital signal sequence (data 301a in FIG. 3) selected by the seed beam switch unit 301 is provided to the preparation unit 302 (FIG. 3).

The preparation unit 302 enables this receiving method to offer characteristics of enough robustness to noise, sonic change, and the like.

The preparation unit 302 is described in more detail later in in Embodiment 4.

In the receiving method according to Embodiment 1, for example, the preparation unit 302 does not need to perform its processing.

In FIG. 3, the preparation unit 302 is shown for the sake of convenience in the description. More specifically, the seed beam forming unit 202x may not include the preparation unit 302, or may include the preparation unit 302 as described in more detail in Embodiment 3 and the like.

Output signal sequences of the preparation unit 302 (or received signal sequences (data 301a) selected by the seed beam switch unit 301 in the case where the apparatus 100 does not include the preparation unit 302) are provided to the delay addition processing unit 303.

The delay addition processing unit 303 performs so-called delay addition operation on the output signal sequence (the preparation unit 302 does not perform anything in Embodiment 1) which corresponds to the receiving element selected by the seed beam switch unit 301 and is provided from the preparation unit 302, thereby forming a seed beam output sequence (data 202b).

The delay addition operation may be, for example, merely a know technique in the related technical field, and more specifically, may be an operation determined by a general equation presented below.

In more detail, when a numeral of the receiving element is i, a pitch between two adjacent elements is d in the case where the receiving element numeral 1 is an element that is the farthest from a target region to be observed (Region of Interest (ROI)), a beam angle is θ (perpendicular to an element sequence in the case where θ is 0), and a sonic speed is c, a delay amount for the receiving element i can be expressed by the following Equation 1.

[Math. 1]
$$\tau_i = \frac{(i-1)d\sin\theta}{c} \quad \text{(Equation 1)}$$

If the received signal sequence of the element i is $x_i$, a delay-and-sum method value of ROI at time t can be expressed by the following Equation 2.

[Math. 2]
$$DAS_{ROI} = \sum_i x_i(t - \tau_i) \quad \text{(Equation 2)}$$

On the other hand, since the seed beam forming unit 202 according to the present invention has the seed beam switch unit 301, a delay-and-sum method value for a ROI of a seed beam P is expressed by the following Equation 3.

[Math. 3]
$$sbm_{ROI}^P = \sum_i \text{sbm\_sw}^P(i) \cdot x_i(t - \tau_i) \quad \text{(Equation 3)}$$

Here, a switch of the seed beam switch unit 301 for the seed beam P is expressed by the following Equation 4.

[Math. 4]
$$\text{sbm\_sw}^P(i) = \begin{cases} 1, & \text{(ON)} \\ 0, & \text{(OFF)} \end{cases} \quad \text{(Equation 4)}$$

It should be noted that any seed beam to be formed is not necessarily formed by intermittently selecting a part of receiving elements by the seed beam switch unit 301. In other words, a part of signals each generated as a seed beam may be a seed beam formed by using all of the receiving elements. More specifically, the formed seed beams may include a seed beam formed by using all of the receiving elements, and a directivity of a part of the beams may be substantially the same as a directivity of the seed beams formed by using all of the receiving elements.

<Beam Synthesis Unit>

Referring back to FIG. 2, the description is given. The seed beam output sequences formed by the respective seed beam forming units 202 are provided to the beam synthesis unit 203.

First, an object and a summary of the beam synthesis unit 203 are described.

An object of the beam synthesis unit 203 is to form (a) a main beam having a high intensity for a target region and (b) a plurality of sub beams having a low intensity for the target region which is weaker than the intensity of the main beam, both of which are to be used by the narrow beam forming unit 203 (FIG. 2) described later.

In short, beams as inputs of the beam synthesis unit 203 are the seed beams as described previously. Therefore, the object of the beam synthesis unit 203 includes forming of a main beam having a narrow directivity with a relatively high intensity for the target region, from one or more seed beams. Then, the object of the beam synthesis unit 203 also includes forming of sub beams having a directivity with a low intensity for the target region in order to cancel noise from regions except the target region, from one or more seed beams.

It should be noted that an example of the sub beams having a directivity with a low intensity for the target region is so-called a null beam which has directivity characteristics of an acoustic blind angle (blind angle not receiving reflection sound).

Here, if a null beam is formed by using seed beams formed by the present embodiment, it is possible to form a beam having a beam directivity with a sharper and narrower blind angle in comparison to a width of a main lobe in delay addition using all of the receiving elements.

Therefore, if arithmetic operations are performed by using a plurality of seed beams, it is possible to achieve a relatively sharp directivity for a plurality of directions.

As a result, it is expected to form a beam having a directivity with a low intensity or null (intensity of 0) for a limited region including the target region.

For each of the seed beams, while a main lobe has a high directivity, side lobes have various levels and various directivities. Therefore, in the seed beam synthesis, not only the main lobe but also the side lobes should be controlled.

Therefore, in order to form the main beam and the sub beams by the beam synthesis unit 203, beams having various directivities are formed based on a plurality of seed beams.

In the beam synthesis unit 203, multiplication, addition, subtraction, or the like is performed on the seed beams, so that not only a main beam but also beams in which side lobes can be controlled (canceled) can be formed.

Figure 7:
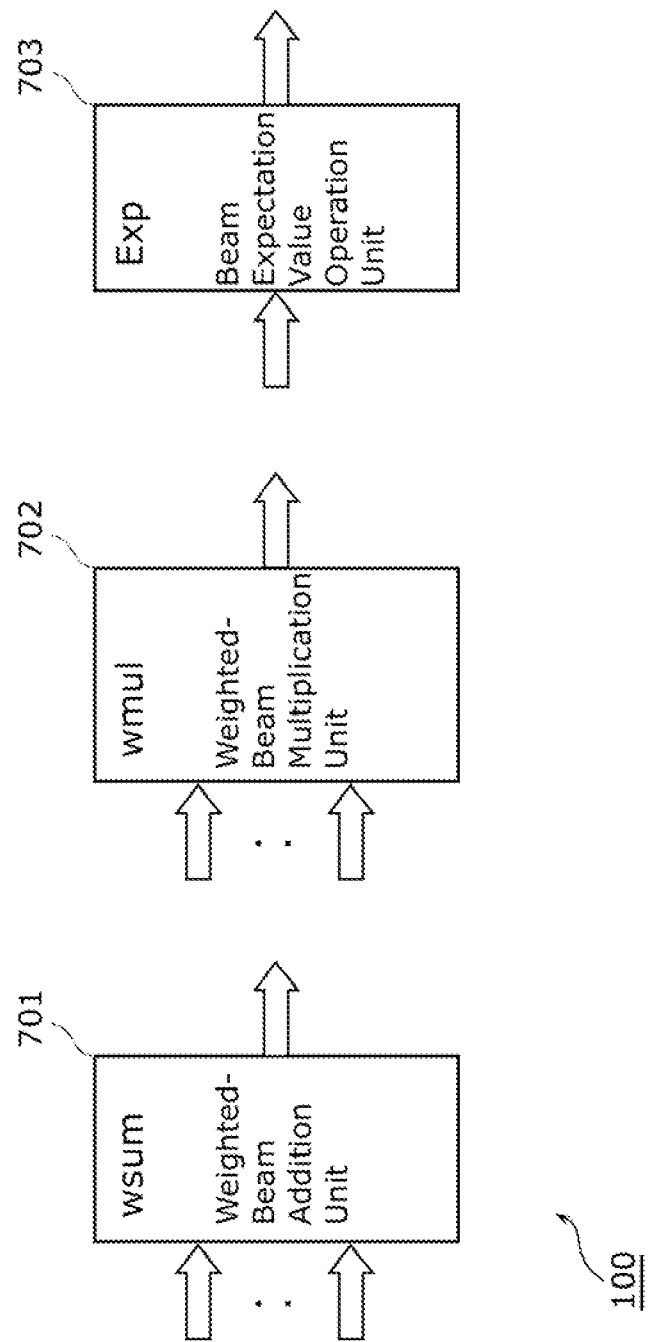
FIG. 7 is a diagram showing an arithmetic operation unit in a beam synthesis unit.
Figure 8:
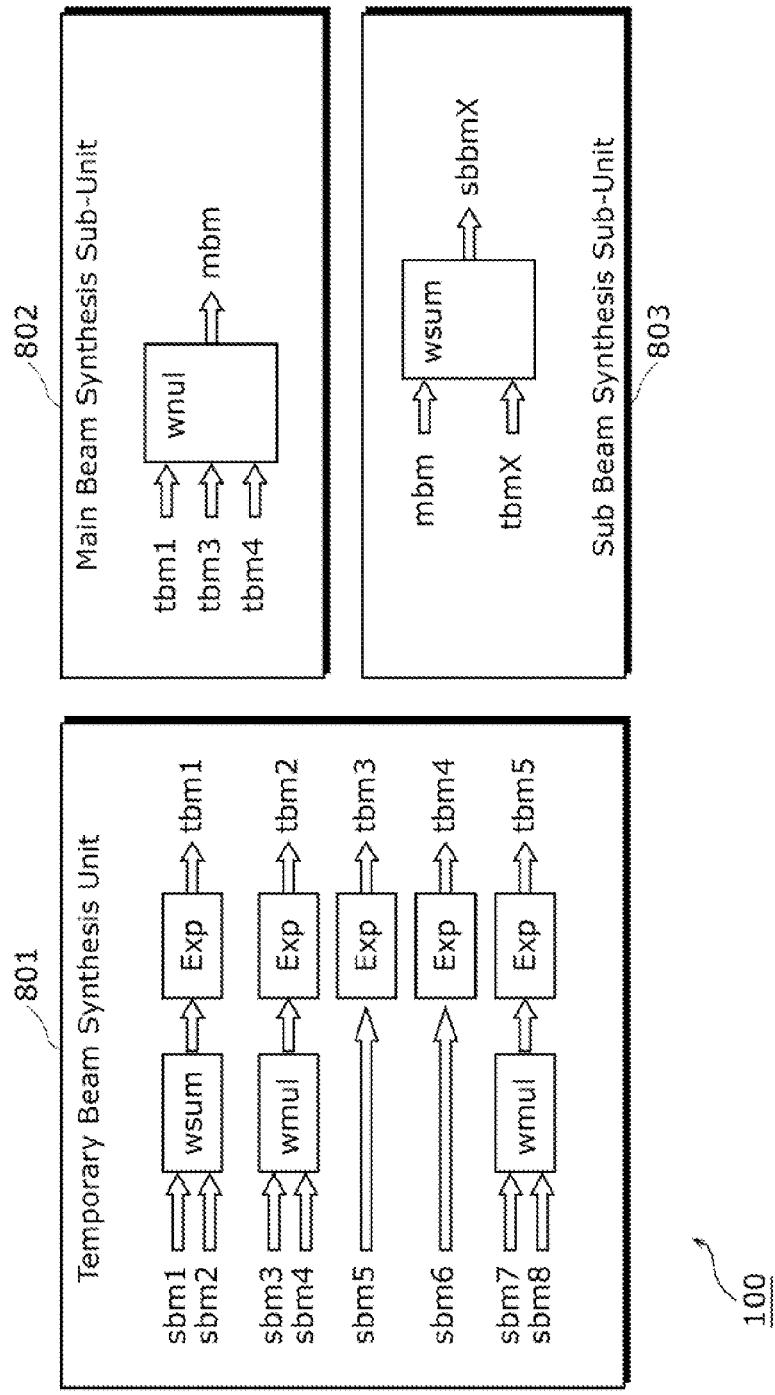
FIG. 8 is a block diagram showing the beam synthesis unit.

A structure and operations of the beam synthesis unit 203 are described in more detail with references to FIGS. 7 and 8.

The beam synthesis unit 203 includes a plurality of beam synthesis sub-units.

FIG. 7 is a diagram showing the apparatus 100.

First, the beam synthesis sub-units are described with reference to FIG. 7.

The beam synthesis sub-units (beam arithmetic operation units) use a plurality of seed beams and a plurality of beams provided from the beam synthesis sub-units as inputs, and perform predetermined arithmetic operations on the input beams.

In addition, if necessary, the beam synthesis sub-units weight the respective input beams by respective weight coefficients to perform arithmetic operations on the beams. The arithmetic operations may be, for example, addition, multiplication, subtraction, or expectation value operation, and the like. Here, weighting means that when operation is performed using a plurality of seed beams, a value (a value of an intensity) of each of the seed beams is multiplied by a corresponding coefficient assigned to the seed beam.

It should be noted that a weight coefficient may be 1 if it is not necessary to weight the input beams.

A weighted-beam addition unit 701, which is one of the beam synthesis sub-units, performs beam synthesis by processing determined by the following Equation 5.

[Math. 5]

$$tbm_{ROI} = WSUM \cdot (sbm_{ROI}^P + sbm_{ROI}^Q) \quad \text{(Equation 5)}$$

A weighted-beam multiplication unit 702 uses a plurality of seed beams and a plurality of synthesized beams provided from the beam synthesis sub-units as inputs, and weights each of the input beams by a corresponding weight coefficient and multiplies the beam by the weight coefficient. The weighted-beam multiplication unit 702 performs the beam synthesis as determined in the following Equation 6.

[Math. 6]

$$tbm_{ROI} = WMUL \cdot sbm_{ROI}^P \cdot sbm_{ROI}^Q \quad \text{(Equation 6)}$$

Using the seed beams and the synthesized beams provided from the beam synthesis sub-units as inputs, a beam expectation value operation unit 703 performs arithmetic operation as determined by the following Equation 7.

[Math. 7]

$$\exp\_sbm^P = \sum_{ROI} sbm^P \cdot sbm^P \quad \text{(Equation 7)}$$

Here, results of the arithmetic operation by the beam expectation value operation unit 703 are used, for example, in adjustment of beam energy and the like in functional blocks not shown.

FIG. 8 is a diagram showing the apparatus 100.

Next, the operations performed by these beam synthesis sub-units are described. The following describes the operations of the beam synthesis units 203 with reference to FIG. 8.

The beam synthesis unit 203 includes a main beam synthesis sub-unit 802 that forms a main beam and a sub beam synthesis sub-unit 803 that forms null beams for the target region. The beam synthesis unit 203 may include also a temporary beam synthesis sub-unit 801 if variations of beams should be increased to form the main beam and the sub beams.

The temporary beam synthesis sub-unit 801 synthesizes temporary beams (for example, tbm1 to tbm5) from 8 kinds of seed beams (for example, sbm1 to sbm8) as inputs, by using above-described weighted-beam addition unit, weighted-beam multiplication unit, and the beam expectation value operation unit. It should be noted that the temporary beam synthesis is not essential in the beam synthesis unit 203, but has advantages that a beam having a high directivity for a predetermined direction can be newly formed by appropriately synthesizing a seed beam from a predetermined number of seed beams.

It is possible that all of the weighting coefficients in the operation units may be the same 1, or also possible that a weighting coefficient is previously assigned as a coefficient for implementation and operation is performed based on the assigned weighting coefficient. It is also possible that the apparatus 100 may have a structure in which a user can select a value of the coefficient.

The main beam synthesis sub-unit 802 synthesizes the main beam (mbm) by using the weighted-beam multiplication unit, from, for example, three temporary beams from among the plurality of temporary beams formed by the temporary beam synthesis sub-unit 801.

For example, the main beam is synthesized from tbm1, tbm3, and tbm4.

However, the main beam synthesis method is not limited to the above-described arithmetic operation method.

The method of the main beam synthesis is not limited to the method using any one of arithmetic operation methods. More specifically, it is possible that, in order to from a main beam having a high directivity for a specific region and a high intensity, it is determined which arithmetic operation(s) from among the plurality of arithmetic operations is/are to be combined, for example, based on a width (for example, a half width value) of a seed beam or the like, and that the main beam synthesis is therefore performed by the method using the determined combination.

Next, the sub beam synthesis sub-unit 803 performs sub beam synthesis by using the main beam (mbm) and a predetermined temporary beam in the weighting addition unit. It should be noted that the sub beam synthesized by using a temporary beam X is referred to as a sub beam X (sbbmX).

It is arbitral whether or not to use a temporary beam in the sub beam synthesis like in the main beam synthesis. Furthermore, the used arithmetic operation method is not limited to any one of arithmetic operations methods. It should be noted that the seed beam may be used directly in the main beam forming and the sub beam forming.

Moreover, in the main beam synthesis, it is not necessary to always use the formed seed beams, but it is also possible to use a signal of one seed beam directly as the main beam.

As described above, the beam synthesis unit 203 increases beam variations more than the variations of the seed beams formed by the seed beam forming unit 202, and then forms a main beam and sub beams by using the various increased beams and, if necessary, the seed beams themselves.

It should be noted in the description of the present invention that the beam synthesis sub-units (beam arithmetic operation units) are described for the sake of the convenience in the description, but it is needless to say that it is enough if the processing performed by the structure is included in the processing calculated on the signal circuit included in the beam synthesis unit 204.

<Narrow Beam Forming Unit>

Next, the narrow beam forming unit 204 (FIG. 2) is described.

The narrow beam forming unit 204 sums the plurality of sub beams formed in the beam synthesis unit 203 to synthesize them into a beam having a beam directivity with a low intensity for the target region in order to cancel noise occurred in regions except the target region.

In the present invention, this beam is referred to as a suppressed beam.

It should be noted that it is also possible to form the suppressed beam by performing weighting arithmetic operation on the plurality of sub beams.

Hereinafter in the description, a coefficient added to the suppressed beam is referred to as a "suppression coefficient".

The main beam has a high intensity for the target region, but is not narrow enough for the target region. Therefore, the narrow beam forming unit 204 forms the suppressed beam, and then subtracts the formed suppressed beam from the main beam. By this method, it is possible to eventually obtain a beam signal having an enough narrow width and a high intensity for the target region.

The eventually generated signal is referred to a narrow beam.

The narrow beam means a signal which has a high directivity and a high intensity for the target region, and has a low directivity and a low intensity for other regions except the target region.

The processing performed by the narrow beam forming unit 204 (FIG. 2) is described with reference to FIG. 9.

The beam synthesis unit 203 provides the narrow beam forming unit 204 with at least the main beam and the sub beams formed in the beam synthesis unit 203.

In addition, if necessary, the temporary beams are also provided.

The beam forming unit 204 uses signals of these input beams to perform beam synthesis appropriately using the above-described beam synthesis sub-units (beam arithmetic operation units) and the like, thereby forming the main beam and the suppressed beam.

For example, the suppressed beam is formed from the sub beams and the temporary beams as inputs by using the weighted-beam addition unit 901.

Here, although the arithmetic operation in forming the suppressed beam has been explained as addition, it is not limited to addition but may be multiplication or a combination of addition and multiplication.

On the other hand, the main beam is inputted into a main beam preparation unit 902, and the main beam preparation unit 902 outputs a corrected main beam.

Hereinafter in the present invention, the output signal of the main beam preparation unit 902 is referred to as a corrected main beam, for the sake of the convenience in the description.

The main beam preparation unit 902 performs adjustment of energy with the suppressed beam, for example.

It should be noted that the suppressed beam may be one of inputs of the main beam preparation unit 902 and be used in the energy adjustment in the main beam preparation unit 902.

Here, the energy adjustment means that arithmetic operation is performed so that total energy of the main beam becomes equivalent to total energy of the suppressed beam, at least in units of order.

It is also possible to perform arithmetic operation so that intensity energy of the main lobe of the main beam becomes equivalent to intensity energy of the main lobe of the suppressed beam, at least in units of order.

If not necessary, it is not necessary to input the seed beams to the main beam preparation unit 902.

It is further possible that the output signals of the weighted-beam addition unit 901 are provided to the main beam preparation unit 902 and energy of the suppressed beam not the main beam is adjusted.

More specifically, it is possible that, for example, the energy adjustment is performed depending on how many stages of the plurality of arithmetic operation units in the beam synthesis unit 203, such as the arithmetic operation weighted-beam multiplication unit and the weighted-beam addition unit, the seed beams have passed to be synthesized into the main beam, or depending on how many stages the suppressed beam has also passed. For example, if the forming of the main beam requires the four operations of the weighted-beam multiplication unit and the forming of the sub beam requires two operations of the weighted-beam multiplication unit, it is possible that the main beam preparation unit 902 can match virtual arithmetic operation order by performing square root operation on the main beam.

The output of the main beam preparation unit 902 which is generated as described above is referred to as a corrected main beam.

Finally, the weighted-beam subtraction unit 803 receives the suppressed beam and the corrected main beam and performs the processing as determined by the following Equation 8 on them to obtain a target barrow beam (data 204a in FIG. 2).

[Math. 8]

$$nbm_{ROI} = mbm_{ROI} - WSUB \cdot sbm_{ROI} \quad \text{(Equation 8)}$$

Here, the weighting coefficients used in the weighted-beam addition unit 801 and the weighted-beam subtraction unit 803 significantly influence a directivity of a resulting barrow beam and a suppressed degree of noise. Therefore, when a predetermined coefficient is to be used, an appropriate coefficient is set so that a stable narrow beam can be offered without burden on the user. Therefore, as the ultrasonic diagnostic apparatus, even if the apparatus draws images, it is possible to provide images with high image quality.

If dynamic learning is performed to determine an appropriate suppression coefficient to be used, it is possible to arrange an adaptive filter at a position where various beams, temporary beams, and signals passing through the respective units 701 are inputted. Under the above situation, the control unit may determine the weighting coefficients by learning. For example, a weighting coefficient to be assigned to a predetermined sub beam is increased, and if a directivity of a narrow beam is improved, then the weighting coefficient is further increased. When the directivity of the narrow beam is getting lower at a certain point, the increase of the weighting coefficient is stopped, and the weighting coefficient is set to have a value between the currently-set weighting coefficient and the previously-set weighting coefficient. In this case, it is expected to offer noise suppression effects and the like which are higher than the situation where a coefficient is estimated separately or the situation where a fixed coefficient is used by performing learning and then using a beam directivity pattern of each of the sub beams and in temporary beams.

If the weighting coefficient can be varied for some groups or for each of groups and the user can select the weighting coefficient, image quality can be adjusted by user's subjective view, not by noise is suppression effects produced by arithmetic operations.

If a plurality of beams can be obtained, it is also possible that weights of the coefficients of the beams are the same and that addition and multiplication are not performed based on the weights. For example, regarding the beams, for the relatively large number of beams used by elements around the center from among elements of an opening formed by the element group, if a weight of such beams is increased, improvement of S/N can be generally expected. More specifically, it is desirable that calculation is performed by weighting heavier for seed beams for which the number of used receiving elements is z (z is a positive integer and z>y) from among x receiving elements (where x is a positive integer) including a receiving element at the center from among the plurality of receiving elements included in the receiving unit 201, than seed beam signals for which the number of used receiving elements is y (y is a positive integer and y≤x−1) from among the x receiving elements. Therefore, it is possible to form a beam relatively strong for noise.

On the other hand, if the number of used receiving elements is large around a maximum opening relatively far from the center, it is possible to form a beam having good suppressed beam characteristics. In other words, there are x receiving elements (where x is a positive integer) at each end of the plurality of receiving elements included in the receiving unit 201. It is desirable that calculation is performed by weighting heavier for seed beams for which the number of used receiving elements is z (z is a positive integer and z>y) from among x receiving elements, than seed beam signals for which the number of used receiving elements is y (y is a positive integer and y≤x−1) from among the x receiving elements.

By appropriately changing a weight for seed beams, it is possible to further improve S/N characteristics of formed beams.

If some weights of the sub beams and the temporary beams are set to 0, by eventually reducing the number of controlled beams, the user can selectively and easily switch desired image quality.

By the receiving method including the processes by the seed beam forming unit 202, the beam synthesis unit 203, and the narrow beam forming unit 204 in FIG. 2, which is so-called a beamforming method, it is possible to obtain beam characteristics with a higher directivity and a better S/N ratio in comparison to the conventionally formed beams.

An ultrasonic apparatus using this beamforming method and an ultrasonic apparatus including a beamforming unit can offer higher-quality image having a higher resolution and more-suppressed noise, in comparison to a conventional ultrasonic diagnostic apparatus using delay-and-sum method.

It should be noted that it has been described in Embodiment 1 that the beam synthesis unit 203 forms a main beam and sub beams, and the narrow beam forming unit 204 performs arithmetic operations on the main beam and the sub beams to synthesize a narrow beam. However it is not necessary to temporarily form the main beam and the sub beams. It is also possible to use a beamformer unit 105 having a structure of forming a narrow beam directly from seed beams (in other words, a combination of the beam synthesis unit 203 and the narrow beam synthesis unit 204, without separating them). More specifically, for example, it is possible that a narrow beam is formed directly from seed beams, without temporarily forming a main beam and sub beams and then forming the narrow beam from the main beam and the sub beams.

Figure 22:
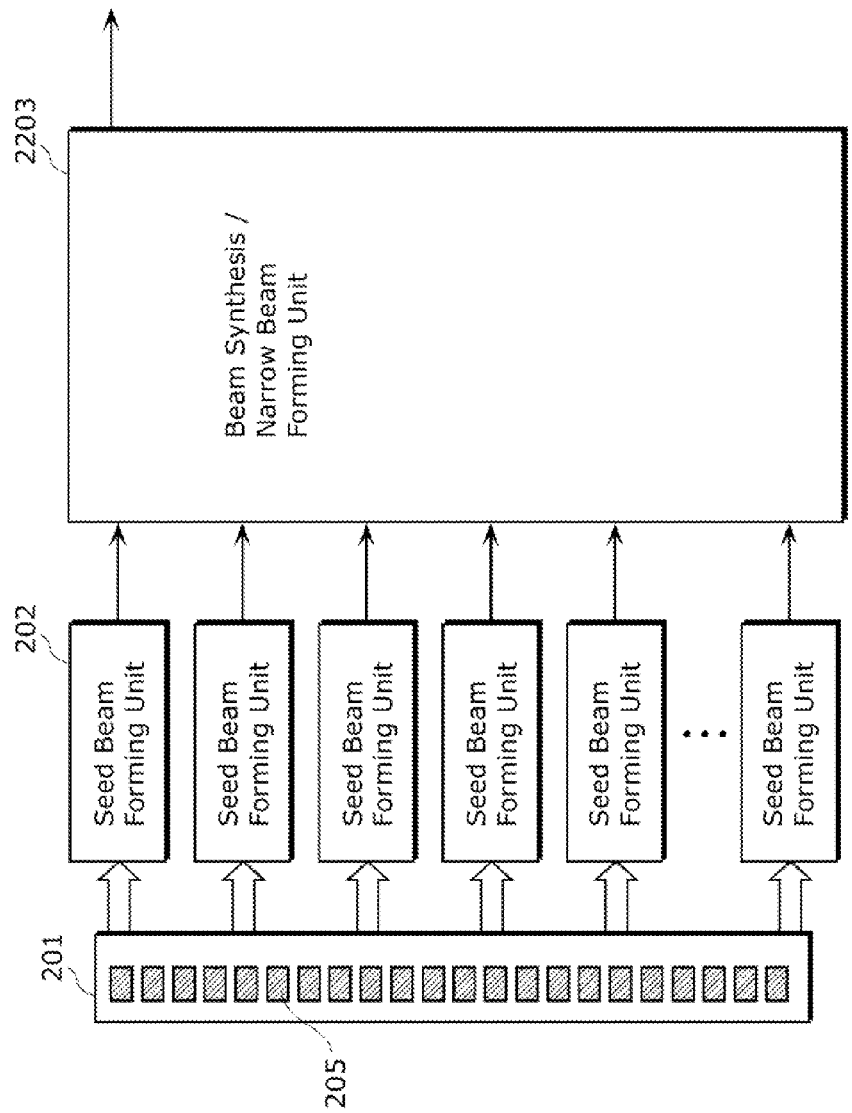
FIG. 22 is a block diagram showing a receiving method of a ultrasonic diagnostic apparatus.

FIG. 22 is a diagram showing a beam synthesis/narrow beam forming unit 2203 and the like.

More specifically, in the structure in this case, as shown in FIG. 22, there are the receiving unit 201, the seed beam forming unit 202, and the beam synthesis/narrow beam forming unit 2203. The receiving unit 201 and the seed beam forming unit 2203 may be the same as shown in FIG. 2. Then, it is possible that only the beam synthesis/narrow beam forming unit 2203 is different from FIG. 2. On the other hand, there is only a difference that a series of processing performed by the beam synthesis unit 203 and the narrow beam forming unit 203 shown in FIG. 2 is performed by the beam synthesis/narrow beam forming unit 2203, and the arithmetic operations themselves may be the same.

It is also possible that, when a combination of used receiving elements is switched by using the seed beam switch unit 301, a receiving opening is set to large if a depth of a target region (a minimum distance from the receiving element sequence to the target region) is relatively deep, and the receiving opening is set to small if the depth is relatively shallow. In other words, it is possible that the seed beam switch unit 301 controls a size of the receiving opening according to the depth of the target region, and accordingly, changes a combination of actually used receiving elements.

For example, there is a situation where there are, as the target regions, a first target region and a second target region that is positioned deeper in a distance from the body surface in comparison to the first target region. In such a situation, the number of openings of the receiving elements which are selected when seed beams are formed for signals from the second target region is set to be larger than the number of openings of the receiving elements which are selected when seed beams are formed for signals from the first target region.

The effects of the above case are followings. When the target region is shallow, even if the receiving opening is large, noise from regions except the target region are collected, and elements that receive received signals available as received signals are limited to elements near the target region. Therefore, a beam having a higher S/N can be formed when the receiving opening is smaller. The effects in the above-described case is forming a beam with a higher S/N.

It should be noted that, as described earlier, when the beam synthesis unit 203 increases variations of beams, it is generally possible to suppress noise from regions except the target region and to form a narrow beam for the target region. Here, the increase of the beam variations results in increase of multiplication and addition operations. On the other hand, regarding the ultrasonic diagnostic apparatus, how many tomographic images the ultrasonic diagnostic apparatus can produce per unit time is an important evaluation index as one of evaluation indexes for image diagnostic information. For the reason, a frame rate as high as possible is generally desired. Therefore, when increase of a frame rate is to be prioritized, beam variations are decreased in an ultrasonic apparatus having a limited arithmetic operation performance to reduce arithmetic operations in a beam-former, thereby increase the frame rate. Furthermore, the frame rate is set so that the number of formed sub beams at the first frame rate is smaller than the number of formed sub beams at the second frame rate that is higher than the first frame rate.

Meanwhile, an ultrasonic diagnostic apparatus having a low arithmetic operation performance is expected to have a difficulty of executing the beam-former at a desired frame rate. In such a case, the number of beam variations is also decreased, so that such an ultrasonic diagnostic apparatus having a low arithmetic operation performance can offer the beam-former according to the present invention.

Embodiment 2

In Embodiment 2, an ultrasonic diagnostic apparatus is described with reference to FIG. 11.

Figure 11:
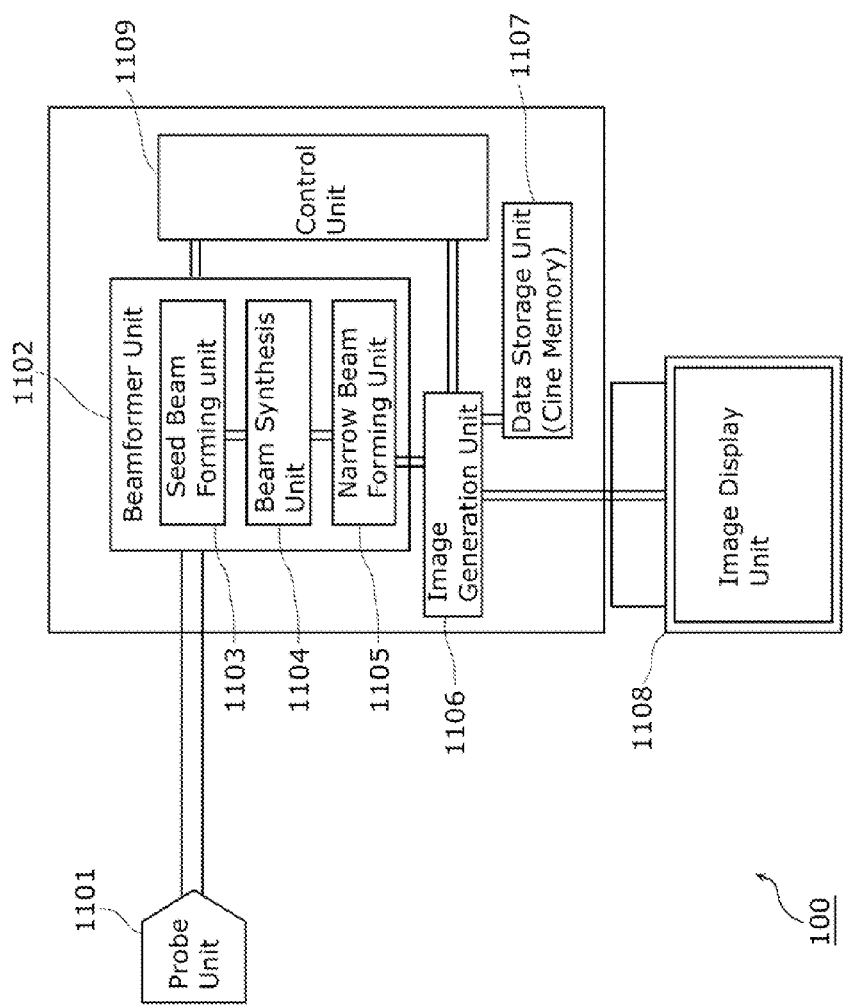
FIG. 11 is a diagram showing an ultrasonic diagnostic apparatus according to a second embodiment of the present invention.

FIG. 11 is a diagram showing the ultrasonic diagnostic apparatus according to Embodiment 2.

A probe 1101 scans a ultrasonic beam for a target object by using, for example, a phased array method or the like, based on signals from a transmitting/receiving unit (not shown).

In the probe 1101, at least one sequence of ultrasound receiving elements arranged in a one-dimensional direction is provided.

The probe 1101 transmits ultrasound and receives reflection signals from the target object, by using a part (or all) of the ultrasound receiving elements arranged in the one-dimensional direction. Here, for the used ultrasound, it is not necessary to use all of the ultrasound receiving elements arranged in the one-dimensional direction.

Figure 10A:
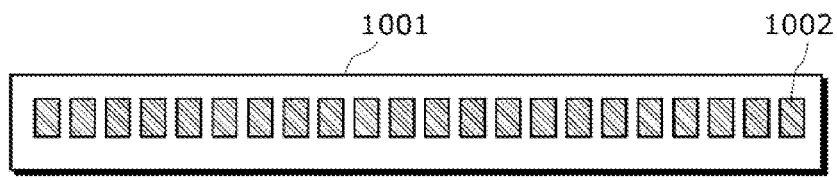
FIG. 10A is a diagram showing the receiving units in the case where all of the receiving units are used.
Figure 10B:
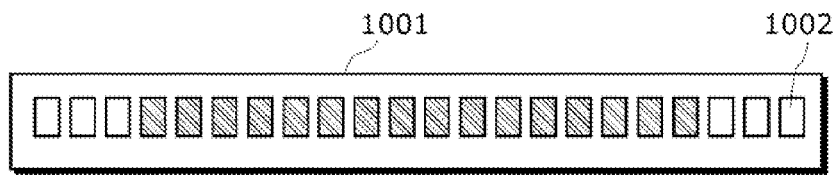
FIG. 10B is a diagram showing the receiving units in the case where a part of the receiving units are used.

Each of FIGS. 10A and 10B shows an example of the receiving elements used in transmitting and receiving ultrasound.

In FIGS. 10A and 10B, the receiving elements used in transmitting and receiving are shown as hatched.

FIG. 10A shows the probe 1101 where receiving elements at both ends are used to have a maximum number of openings.

On the other hand, for example, as shown in FIG. 10B, it is also possible that receiving elements at both ends are not used but only necessary receiving elements in a predetermined region are used.

It should be noted that the ultrasonic diagnostic apparatus according to the present embodiment may be any as long as it can output an image of the target object by using signals provided from the probe 1101, and may not include the probe 1101.

Next, received signals of the probe 1101, which are so-called echo signals, are provided to the beamformer unit 1102. The echo signals provided to the beamformer unit 1102 are first processed in the seed beam forming unit 1103. In this processing, a plurality of seed beams are formed from the provided echo signals.

The seed beam forming, unit 1102 selects signals to be used for seed beam forming, from the signals generated by the respective receiving elements.

For example, in order to form a first seed beam (seed beam 1) included in the formed seed beams, it is possible to use a signal pattern as shown at the leftmost (the 1st column in Table 6T) in FIG. 6 (as described previously). Then, in order to form a second seed beam (seed beam 2), signals of the receiving elements are used by a pattern as shown in the second from the left (the 2nd column in Table 6T).

It should be noted that how many kinds of patterns are to be used to form seed beams is arbitrary, but at least two kinds of patterns are used to form at least two kinds of seed beams.

The selection pattern of signals of the receiving elements is also arbitrary, but the resulting seed beams have the following characteristics. A width of a main lobe of a formed seed beam is narrower than a width of a main love of a beam formed by using signals obtained by all of the receiving elements. The narrower width of the main lobe means that at least a width of a bottom of the main lobe, or a width at an intensity lower than a peak intensity by 10 dB (not limited to this value) is narrower.

It should be noted that an actual structure for forming seed beams is not limited to any one of structures. For example, it is also possible that a signal circuits that forms respective seed beams is connected with a switching unit that switches signals from used receiving elements, and the switching unit perform switching for each seed beams to switch signals to be used. It is further possible that the control unit 1109 connected to the beamformer unit 1102 appropriately allocates input signals to respective signal circuits that form respective seed beams.

Next, a plurality of seed beams formed by the seed beam forming unit 1102 are provided to the beam synthesis unit 1104. From the input seed beams, the beam synthesis unit 1104 forms (a) a main beam having signal characteristics with a high signal intensity from the target region and a high directivity, and (b) sub beams having a low signal intensity from the target region and a low directivity.

The plurality of beams including the main beam and the sub beams which are formed by the beam synthesis unit 1104 are provided to the narrow beam forming unit 1105. Then, the narrow beam forming unit 1105 performs arithmetic operations on the plurality of beams including the main beam and the sub beams. The arithmetic operations produce a narrow beam which has a high signal intensity of the target region and from which signals of regions around the target region are cancelled. The arithmetic operations are performed to appropriately cancel the signals of regions around the target region from the main beam.

Next, the narrow beam formed by the beamformer unit 1102 is provided to an image generation unit 1106.

The image generation unit 1106 performs predetermined signal processing on the received signal provided from the beamformer unit 1102 so as to generate a fault image. For example, the image generation unit 1106 performs A/D conversion and the like on the electrical signals provided from the transmitting/receiving unit to generate a grayscale fault image, which is, for example, image data of 128 pixels×2000 pixels (luminance resolution of about 10 bits per pixel), for one scanning by the receiving element group.

It should be noted that ultrasonic diagnostic apparatus may include: a normalization unit that normalizes the fault image generated by the image generation unit 1106 to achieve luminance value distribution of a predetermined range; a real time control unit that assures real-time diagnosis; a three-dimensional (3D) image construction unit that combines a plurality of fault images generated by the image generation unit 1106 to generate a 3D image specified by the fault images; or the like, although these units are not shown in FIG. 11.

Furthermore, ultrasonic diagnostic apparatus may include a data storage unit 1107 (cine memory) in which the fault image generated by the image generation unit 1106 is temporarily stored.

For example, the normalization unit performs processing for keeping a dynamic range of the luminance value distribution of the fault image as being steady, processing for keeping dispersion within a predetermined value, and the like.

Furthermore, a memory, an MPEG encoder, and the like may be provided so that, every time a new fault image (normalized fault image) is generated by the data storage unit 1107, the image generation unit 1106, and the above-described normalization unit, an image group including a plurality of such fault images is directly stored as video or is compressed and coded to be stored as video.

The data storage unit 1107 may serve as the following. If continuous sampling of fault images is performed at a high frame rate so that subsequent processing cannot be performed in real time, the data storage unit 1107 temporarily stores image data without losing it and then performs image display and image processing (outline extraction and the like) in due course. The data storage unit 1107 may serve as a data recording device to realize the above.

For example, although a frame rate of general ultrasonic diagnostic apparatuses is 10 to 30 frames per second, it is demanded to achieve 60 or more frames per second in the recent cardiocirculatory medical fields. Therefore, fault images of a few beats are continuously sampled at a high speed and temporarily accumulated, and later screening is performed.

Moreover, the real time control unit is an interrupt control circuit or the like which repeatedly issues a trigger to each constituent unit and includes a frame rate control unit, so that operations of the image generation unit 1106 and the image display unit 1108 are repeated in synchronization with each other at a predetermined frame rate (for example, 30 frames per second).

The frame rate control unit detects a processing state (completion or not) of each constituent unit, or monitors an available capacity of an internal memory or the like to detect the state where allowance more than certain standard is not assured in processing of any of the constituent units. Then, if such detection is made, the frame rate control unit performs rate adjustment to, for example, lower the frame rate.

Therefore, if, for example, a fault image having a large processing load occurs in an unexpected fashion or processing repeatedly occurs, the frame rate is lowered, which makes it possible to prevent partial as missing of the fault image or error such as volume measurement failure.

Next, the fault image generated by the image generation unit 1106 is provided to the image display unit 1108.

The image display unit 1108 includes a graphics accelerator, a scan converter, and the like to display, on a display device, image such as a fault image, video, outline obtained from the image generation unit 1106.

It should be noted that the image display unit 1108 may not be included in the ultrasonic diagnostic apparatus, but may be an external structure. It is also possible that the ultrasonic diagnostic apparatus includes a digital output unit that includes a parallel interface circuit or the like and provides various images, volumes, and the like which are obtained from the image generation unit 1106 as digital signals to an external apparatus such as a personal computer.

The ultrasonic diagnostic apparatus according to the present embodiment forms seed beams which have a high directivity and at least two kinds of directivity patterns. Then, the ultrasonic diagnostic apparatus according to the present embodiment uses the seed beams to form a main beam having a high directivity for a target region and sub beams having a low directivity for the target region, and performs arithmetic operations on these beams to eventually generate electrical signal which has a high directivity for the target region and a suppressed signal intensity for regions near the target region. The signal is used to generate an image with clearer contrast and high image quality.

For example, in a certain aspect or the like, the apparatus 100 (the ultrasonic diagnostic apparatus, see FIGS. 1, 25, etc.) may perform the following processing.

The image display unit 107 may display an image 106*a* (FIG. 1).

At a position of an observation point 101*s* where observation is performed in an observation target (subject) 101*x* such as a body in the displayed image 106*a*, data of the observation point 10*s* may be displayed.

For example, it is possible that color, hue, or the like at the position in the image 106*a* is hue or the like indicating the data, so that the data is displayed at the position.

Then, it is possible that an echo signal (signal 205*a* in FIGS. 2 and 25) that is reflection waves from the observation point 101*s* is received by each of the receiving elements 109 (FIG. 25) provided in the probe unit 101.

It should be noted that, for example, a value of an echo signal received when there is a relatively hard object at the observation point 101*s* is different from that in the case without such a hard object.

The above-described displayed data may be data specified by the plurality of the received echo signals.

Figure 25:
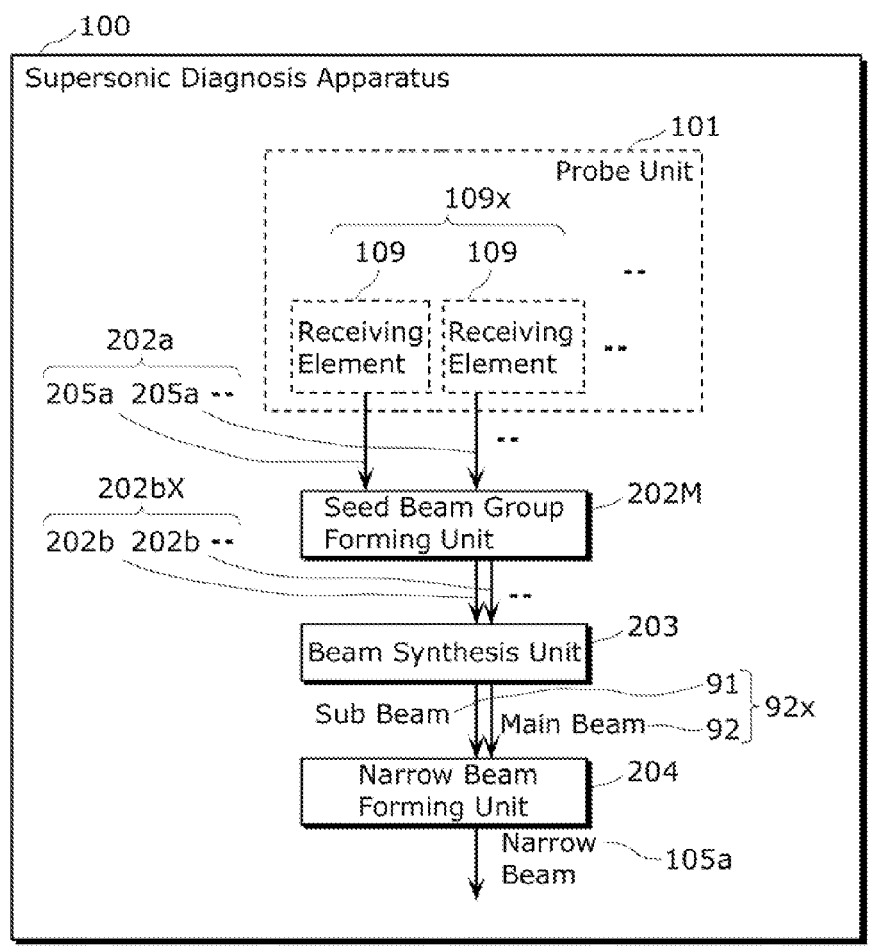
FIG. 25 is a block diagram of the technique according to the present invention.

It is possible to generate the signal (generated signal, narrow signal, narrow beam) 105*a* shown in FIGS. 25, 1, and the like to indicate this data.

The data indicated by the resulting generated signal 105*a* may be displayed at the above-described position in the image 106*a*.

However, the following first signal and second signal can be considered.

There is a signal intensity (see the vertical axis of each graph in FIGS. 4B and 5B) at a corresponding angle (see the horizontal axis of each graph in FIGS. 4B and 5B) of the signal (the above-described generated signal 105*a* or the like).

The above-described angle refers to an angle 101*r* from a front direction 101*p* (FIG. 1) in viewing from the probe unit 101 towards the target point 101*s* (FIG. 1 or the like).

For a range of such an angle, there are a main lobe range (the range 81*m* in FIG. 4B, the range 82*m* in FIG. 5B, etc.) and a side lobe range (the range 81*s* in FIG. 4B, the range 82*s* in FIG. 5B, etc.).

It should be noted that the main lobe range is, as seen in FIGS. 4B and 5B, a range with an angle having an intensity equal to or higher than a predetermined ratio (60/80=0.75 in FIG. 4B, namely, ratio of 75%) in respect with a peak intensity (the intensity 81*h* in FIG. 4B, the intensity 82*h* in FIG. 5B, etc.), for example.

The side lobe range refers to a range except the above-described main lobe range.

It should be noted that, for example, an angle (horizontal axis) of the peak intensity (the intensity 81*h*, the intensity 82*h*, etc.) is an angle of the above-described front direction 101*p*, for example.

In other words, the above-described first signal is a signal generated from the signals 205*a* provided from all of the receiving elements 109. For example, a value (intensity) of the signal is a value (averaged value) generated by summing values of all of the signals 205*a* (see FIG. 4A) (see a signal 2103*x* or the like which is an addition result in the conventional example (example of the delay-and-sum method) in FIGS. 4B and 21).

Such a first signal is as following.

A width (length in a horizontal axis direction of the range 81*m*) of the main lobe range (the range 81*m* in FIG. 4B) of such a first signal is relatively large (long).

Therefore, if the above-described generated signal 105*a* is such a first signal (see the conventional example in FIG. 21), data indicated by the generated signal 105*a* is data specified by pieces of data at respective angles in the relatively large width, so that resolution of the above-described image 106*a* displaying the indicted data is lowered.

Figure 21:
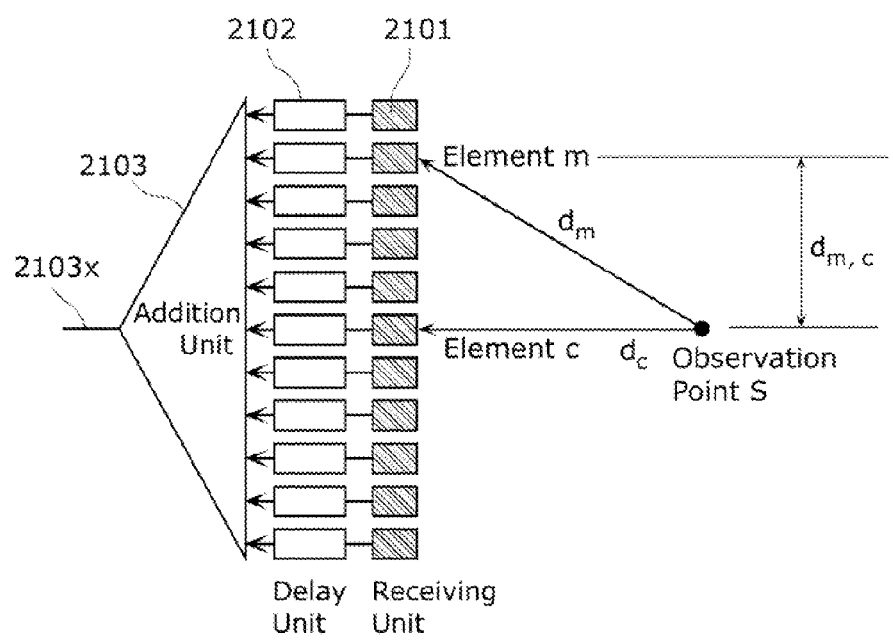
FIG. 21 is a diagram showing the conventional beamforming method.

It is therefore prevented that the generated signal 105*a* is such a first signal (see the conventional example in FIG. 21).

Therefore, a plurality of the signals (seed beams) 202*b* (FIGS. 25, 2, and the like) are generated.

The plurality of receiving elements 109 are arranged at respective positions in order on a straight line 101L (FIG. 4A). On the straight line 101L, the plurality of receiving elements 109 are arrayed.

It should be noted in FIG. 4A that a relatively short arrow line is schematically seen as an arrow line for the straight line 101L for the sake of convenience showing the figure.

It should also be noted that the straight line 101L is, for example, perpendicular to the direction 101*p* (front direction) from the probe to the observation point 101*s*.

Then, the plurality of receiving elements 109 include two receiving elements 109 at both ends, which are a receiving element 101*g* at one of the farthest ends (for example, the top in FIG. 4A) of the straight line 101L and a receiving element 101*h* at the other farthest end (the bottom in FIG. 4A).

For a combination of one or more receiving elements 109, there is the following example (combination in FIG. 5A and the like).

There is a combination in which one or more receiving elements 109 included in the combination do not include one or more receiving elements 109 (the receiving element 101*i* and the like in FIG. 5A) located between the above-described two receiving elements 109 at both ends.

For example, the above-described one or more receiving elements 109 included in the combination are one or more receiving elements 109 including the above-described two receiving elements 109 at both ends.

The above-described generated signal 105*a* (seed beam) is a signal generated from the signals 205*a* (FIG. 25 or the like) of the respective receiving elements 109 included in such a combination that does not include one or more receiving elements 109.

More specifically, a value (intensity) of the generated signal 105*a* may be a sum of values of the respective signals 205*a* in the combination, or may be a sum of values generated by multiplying each value of the respective signals 205*a* by a corresponding coefficient.

Therefore, two or more different signals 205*a* (seed beams) are generated from two or more different combinations.

In the above manner, a signal group 202*a* (FIG. 25) including two or more signals 205*a* is generated.

The number of the generated signals 205*a* (seed beams) may be 5 or 6, for example. Experiments have confirmed that appropriate processing is performed even with such relatively small number of the generated signals 205*a* as described above.

Then, from the two or more signals 205*a*, a signal (main signal, main beam) 92 and signals (sub signals, sub beams) 91 are generated (see FIG. 25 or the like).

It should be noted that each of the main signal 92 and the sub signals 91 may be one of the two or more generated signals 205*a* (seed beams), for example.

It should also be noted that generation of the main signal 92 and the sub signals 91 may refer to obtaining of the signal 205*a* (seed beam) in from the two or more generated signals 205*a* (seed beams), for example.

It should also be noted that a value of each of the main signal 92 and the sub signals 91 may be a sum (average value) of values of one or more signals 205*a* from among the two or more signals 205*a* (seed beams), for example.

It should also be noted that a value of each of the main signal 92 and the sub signals 91 may be a sum of values generated by multiplying each value of one or more signals 205*a* by a corresponding coefficient, for example.

Figure 9:
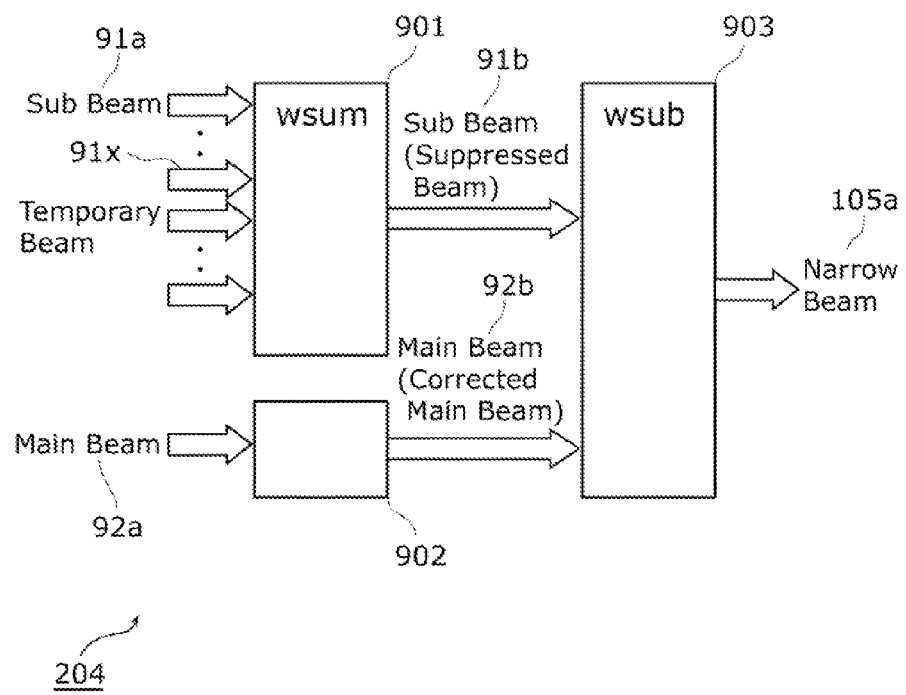
FIG. 9 is a block diagram showing a narrow beam forming unit.

There is a first subtracted signal (for example, the generated signal 105*a* in FIG. 9) having a value (intensity) of the signal which is a value (intensity) generated by subtracting a value of the generated sub signal 91 (the sub signal (sub beam) 91*b*) from a value of the generated main signal 92 (for example, the main signal (main beam) 92*b* in FIG. 9).

It should be noted that, more specifically, as shown in FIG. 9, it is possible to perform the subtraction from, as the main signal 92, a corrected main signal 92*b* from among a main signal 92*a* having a relatively low accuracy prior to correction and the main signal 92*b* having a relatively high accuracy after the correction.

Likewise, as shown in FIG. 9, it is possible to perform the subtraction from, as the sub signal 91, a corrected sub signal 91*b* from among a sub signal 91*a* having a relatively low accuracy prior to correction (modification, adjustment) and the sub signal 91*b* having a relatively high accuracy after the correction.

For such a first subtracted signal, two or more kinds of the first subtracted signals are considered.

Here, one of the first subtracted signals is a coefficient includes in each of the above-described coefficients to be multiplied in calculating the above-described sum that is a value of the sub signal 91 to be subtracted from the main signal 92.

The other of the first subtracted signals has a coefficient with a value that is different from that of the previously-described first subtracted signal. An example of this first subtracted signal is a signal generated by subtracting the sub signal 91 that is the sum using the coefficient having the different value.

Then, it is confirmed that such two or more first subtracted signals include the following second subtracted signal (generated signal 105*a* in FIG. 9). In short, it is confirmed that the second subtracted signal is included in most cases (common cases).

The second subtracted signal is a signal having a main lobe range (see the range 82*m* in FIG. 5B) with a width that is narrower than the width of the main lobe range 81*m* of the above-described first signal generated from the signals 205*a* of all of the receiving elements 109.

Furthermore, the second subtracted signal is an adequately low signal having a side lobe range (see the range 82*s*) with an intensity (for example, an average value of the intensity) that is equal to or lower than the intensity of the side lobe range 81*s* of the above-described first signal generated from the signals 205*a* of all of the receiving elements 109.

This means that the above-described second signal is a relatively appropriate first subtracted signal (second subtracted signal) having a main lobe range with a narrow width and a side lobe range with an adequately low intensity, from among the above-described two or more first subtracted signals.

More specifically, a generated signal 105*a* (narrow signal, narrow beam: FIGS. 1, 9, 25, and the like), by which the above-described data that is generated and indicated by the signal is indicated in the image 106*a*, is such a second signal.

It is thereby possible to decrease the width of the main lobe range of the generated signal 105*a* and therefore increase resolution of the image 106*a*.

Moreover, the above-described signal, which is the appropriate second subtracted signal, is a signal having a main lobe range with a narrow width and also having a side lobe range with an adequately low intensity.

Therefore, although the resolution is increased and the width of the main lobe range of the generated signal 105*a* is decreased, an intensity of the side lobe range is kept adequately low.

It is thereby possible to prevent that inadequately low intensity of the side lobe range increases noise included in the generated signal 105*a*. As a result, it is possible to prevent the increase of the noise included in the above-described image 106*a* generated from the generated signal 105*a*.

In short, noise of the generated signal 105*a* can be reduced, and therefore noise included in the image 106*a* can be reduced.

As a result, both the high resolution and the noise reduction can be achieved.

It should be noted that the main signal 92 may be, for example, a signal generated from a combination of inconsecutive receiving elements not including the above-described one or more receiving elements 109 (the receiving element 101*i* and the like in FIG. 5A) arranged between the two receiving elements 109 at the both ends (see the two receiving elements 101*g* and 101*h* in FIG. 4A).

This means that the main signal 92 may be a signal generated by summing (averaging) signals 205*a* (FIG. 25) of respective receiving elements 109 included in such a combination, for example.

It should also be noted that the main signal 92 may be, for example, a signal generated by summing (averaging) signals 205*a* of all of the receiving elements 109. The above is understood with reference to the signal 2103x in FIG. 21 showing the above-described conventional example and the like, if needed.

Thereby, the main signal 92 is converted to a signal generated from signals 205a of the adequate number of receiving elements 209, which makes it possible to increase stability and accuracy of the main signal 92.

An experiment have been conducted to estimate that the resolution according to the present invention is higher than the resolution of the conventional example.

In the experiment, an observation target 101x (FIG. 1) which is to be observed is two wires arranged to be parallel with each other.

Figure 26A:
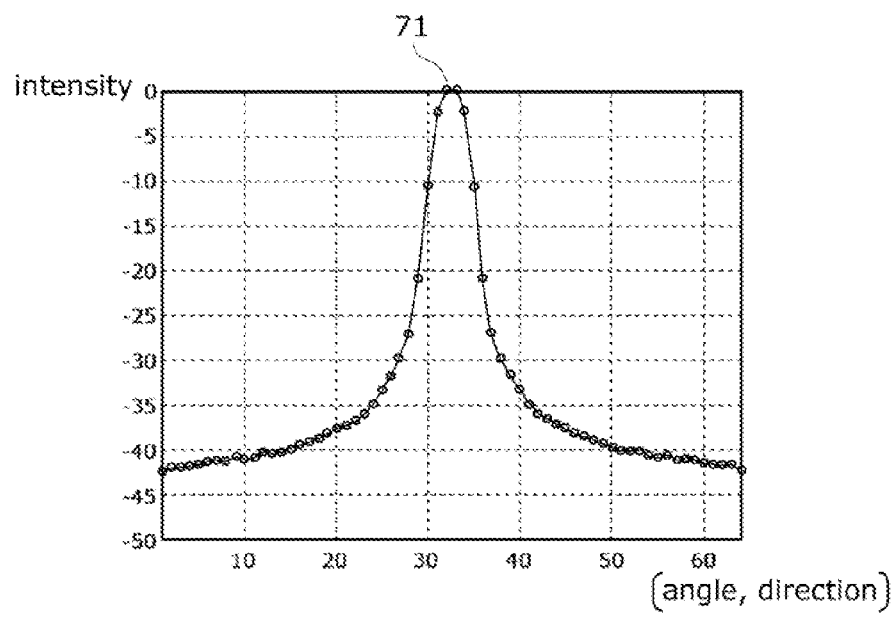
FIG. 26A is a graph plotting processing of the conventional example.

FIG. 26A is a diagram showing a graph of an intensity according to the conventional example shown in FIG. 21.

Figure 26B:
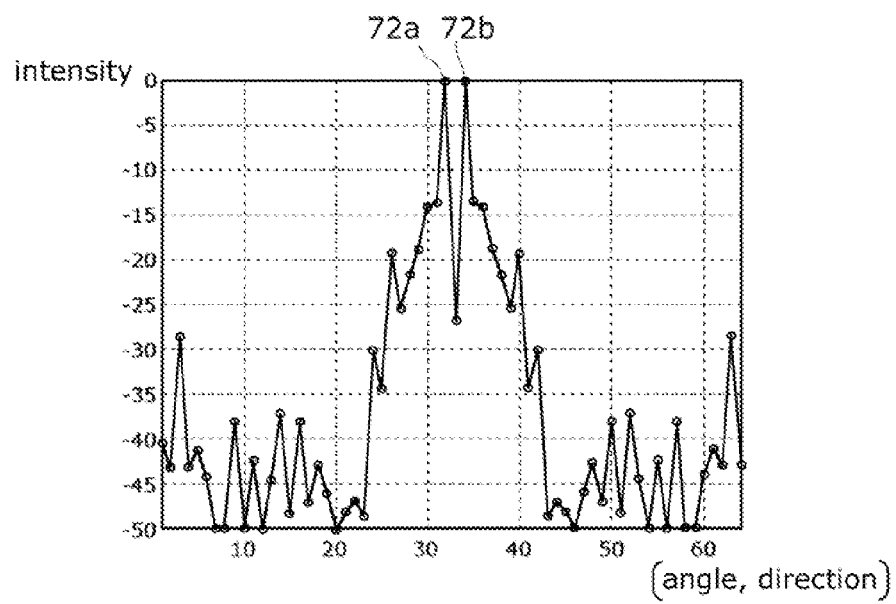
FIG. 26B is a graph plotting processing of the technique according to the present invention.

FIG. 26B is a diagram showing a graph of an intensity according to the present invention.

In the present invention (FIG. 26B), a peak 72a of a signal intensity of one of the wires is observed, and a peak 72b of an intensity of the other wire at an angle close to the angle 101r (see FIG. 1, the horizontal axis of the graph) of the signal 72 is also observed.

On the other hand, in the conventional example (FIG. 26A), two peaks (see the peaks 72a and 72b in FIG. 26B) corresponding to the two wires, respectively, are not observed, but only one peak 71 is observed.

Therefore, the experiment confirms that the present invention can offer resolution higher than that of the conventional example.

Embodiment 3

In Embodiment 1, it has been described that the ultrasonic receiving elements of the ultrasonic probe and the receiving elements are one-dimensionally arrayed. However, the ultrasonic receiving elements in the ultrasonic probe and the receiving elements in the receiving unit 201 may be arranged in a plurality of columns. It is also possible that the ultrasonic receiving elements and the receiving elements may be arranged in a two-dimensional array.

Figure 12:
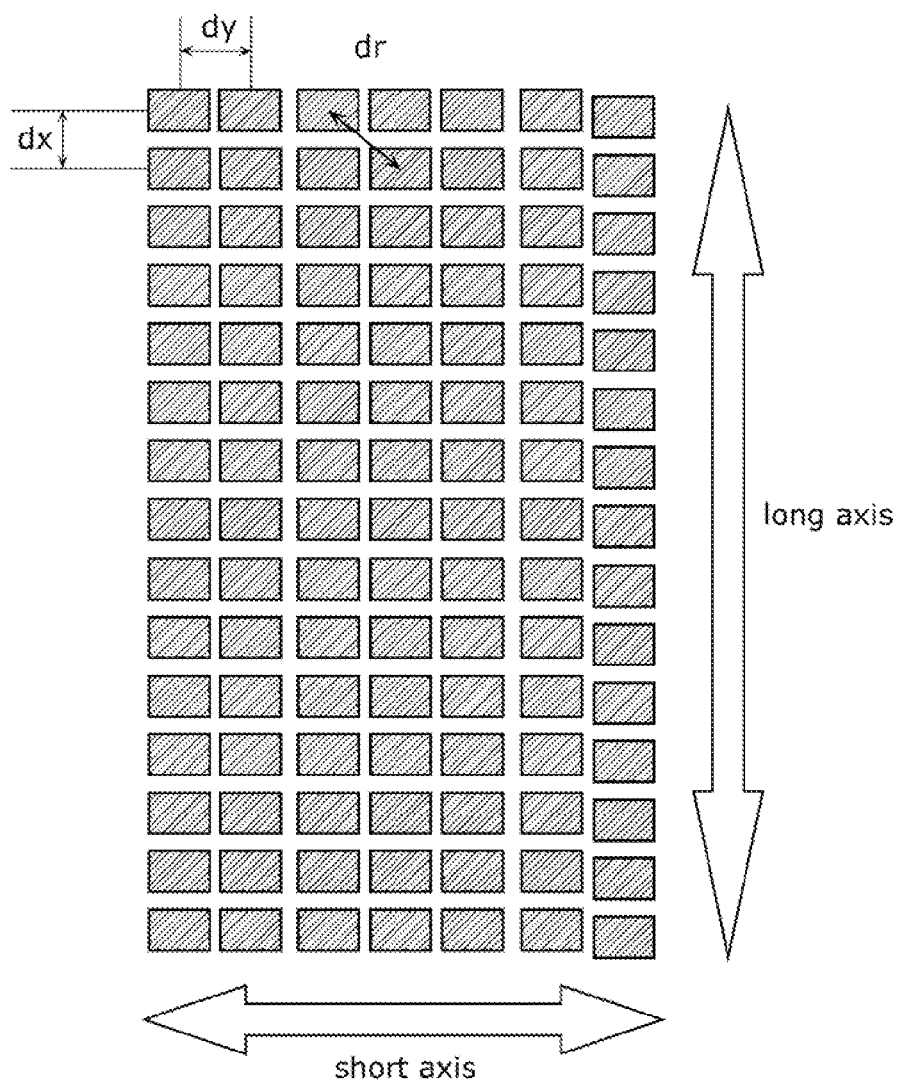
FIG. 12 is a diagram showing an example of a two-dimensional probe.

FIG. 12 is a diagram showing the ultrasonic probe in which the ultrasonic receiving elements are two-dimensionally arranged.

An example of such probes in which elements are two-dimensionally arranged is called a 1.25D probe or 1.5D probe by those ordinarily skilled in the art. This probe is characterized in that there are sequences of probe elements in two axises called a long axis and a short axis, and that the most of probes of existing ultrasonic diagnostic apparatuses have 128 or 192 sequences of elements in the so-called long axis and some columns, such as 5 or 7 columns, in the so-called short axis.

If the short axis has 5 or 7 columns or columns that are much fewer than sequences (rows) in the long axis, the number of combinations of receiving elements for seed beams in the short-axis direction according to the present invention is limited.

However, even with the limited combinations, it is possible to efficiently form seed beams according to the present invention, and as a result, possible to form an appropriate narrow beam.

The following description does not distinguish between probes in which a plurality of ultrasonic receiving elements for which receiving elements are one-dimensionally arrayed are arranged in a plurality of columns and probes in which the ultrasonic receiving elements are arranged in a two-dimensional array. Two sides included in the ultrasonic receiving element group are called a long side and a short side. It should be noted that if the number of arrayed elements is the same and the length of the two sides is the same, the long axis is read as the first axis and the short axis is read as the second axis.

In the case of using the ultrasonic probe according to the present embodiment, the following plurality of patterns are considered depending on whether to apply the beamforming method according to Embodiment 1 to the long axis or the short axis.

(1) Pattern where the beamforming method according to Embodiment 1 is applied to the beamforming in the long-axis direction, and the delay-and-sum method is applied to the beamforming in the short-axis direction.

(2) Pattern where the beamforming method according to Embodiment 1 is applied to the beamforming in the short-axis direction, and the delay-and-sum method is applied to the beamforming in the long-axis direction.

(3) Pattern where the beamforming method according to Embodiment 1 is applied to both in the long-axis direction and the short-axis direction.

In Pattern (1), while signals of respective receiving elements are used in the long-axis direction, beamforming is performed for each column by using the beamforming method according to Embodiment 1. By the processing, a beam is formed for each column in the long-axis direction, and beamforming points are arrayed along the short-axis direction. Next, an intensity of each of the beamforming points is provided to the beamforming unit in the short axis, then delay-and-sum method is performed by using all of the beams arrayed in the short-axis direction, and eventually beams from a target region are formed. In this case, it is desirable that there is at least one beam which is not used in the beamforming between beams used in the beamforming.

It is also possible that the delay-and-sum method in the short-axis direction is first performed, and then the beams from the target region are formed by using a part of the beams arrayed in the short-axis direction for which the delay-and-sum method has been performed. In short, beams are first formed in the short-axis direction by the delay-and-sum method. The beamforming points are arrayed in the long-axis direction. Next, in the long-axis direction, an intensity of each of the beamforming points is replaced by a signal obtained by the receiving element in the receiving unit 201, and then the beamforming is performed in the same manner as described in Embodiment 1.

In Pattern (2), the long axis is replaced by the short axis and the short axis is replaced by the long axis in the above-described Pattern (1). Therefore, Pattern (2) is not described in detail.

Likewise Pattern (3), it is possible to apply the beamforming method according to Embodiment 1 both in the long-axis direction and the short-axis direction.

Figure 13:
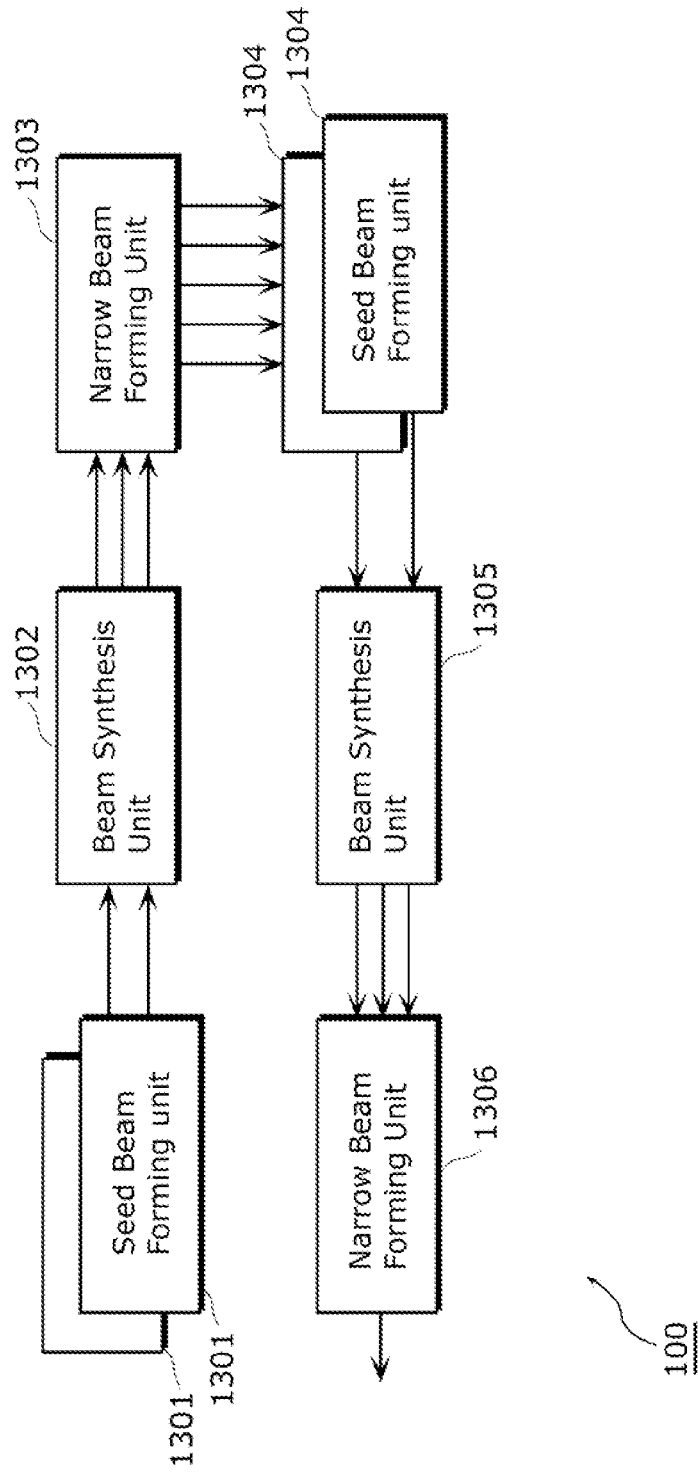
FIG. 13 is a diagram showing an example of a beamforming method according to a third embodiment of the present invention.

FIG. 13 is a diagram showing an example of a beamforming method according to a third embodiment of the present invention.

For example, in the case where the beamforming in the short-axis direction is first performed, each of the seed beam forming units 1301 forms a seed beams by using received signals provided from the receiving elements arrayed in the short-axis direction. This case is characterized by forming a seed beam by using signals of a part of the receiving elements. It is desirable for a part of seed beams that there is a receiving element which is not used in the seed beam forming and located closer to the center than a receiving element which is one of receiving elements used in the seed beam forming and located closest to the end among the receiving elements.

Next, the beam synthesis unit 1302 forms a main beam and sub beams in the short-axis direction, and the narrow beam forming unit 1303 performs beamforming in the short-axis direction. Since the beamforming is performed for each column in the short-axis direction, a plurality of beamforming points are arranged along the long-axis direction after the beamforming.

Next, for each of the plurality of seed beam forming units 1304, a seed beam in the long-axis direction is formed by using a part of these beamforming points. Likewise the beamforming in the short-axis direction, it is desirable that there is a beamforming point not used in the seed beam forming between two beamforming points located the closest to the both ends among from the used beamforming points. After that, by using the seed beams, the beam synthesis unit 1305 and the narrow beam forming unit 1306 perform the beam synthesis and the narrow beam forming, respectively.

Since the processing for the narrow beam in the long axis is performed after performing the processing for the narrow beam in the short axis as described above, variations in the narrow beam forming are increased. Therefore, it is expected that the narrow beam for the target region can produce effects more appropriate than that in the case of using only the 1D probe.

It should be noted that the processing for forming the narrow beam in the short-axis direction may be performed after forming the narrow beam in the long-axis direction. In this case, the maximum number of openings in the short-axis direction is inevitably small. Therefore, it is desirable that a seed beam is formed by using the both ends of the narrow beam in the long-axis direction when the narrow beam in the short-axis direction is formed.

With the above structure, it is possible to perform the beamforming not one-dimensionally but two-dimensionally. This achieves narrow beam forming that is more appropriate than the case of one-dimensional beamforming. As a result, it is expected to offer more appropriate quality of both resolution and noise reduction.

It should be noted that it has been described in the present embodiment that the narrow beam forming is performed in the long axis and the short axis of the ultrasonic receiving elements, but the present invention is not limited to this embodiment.

Figure 14:
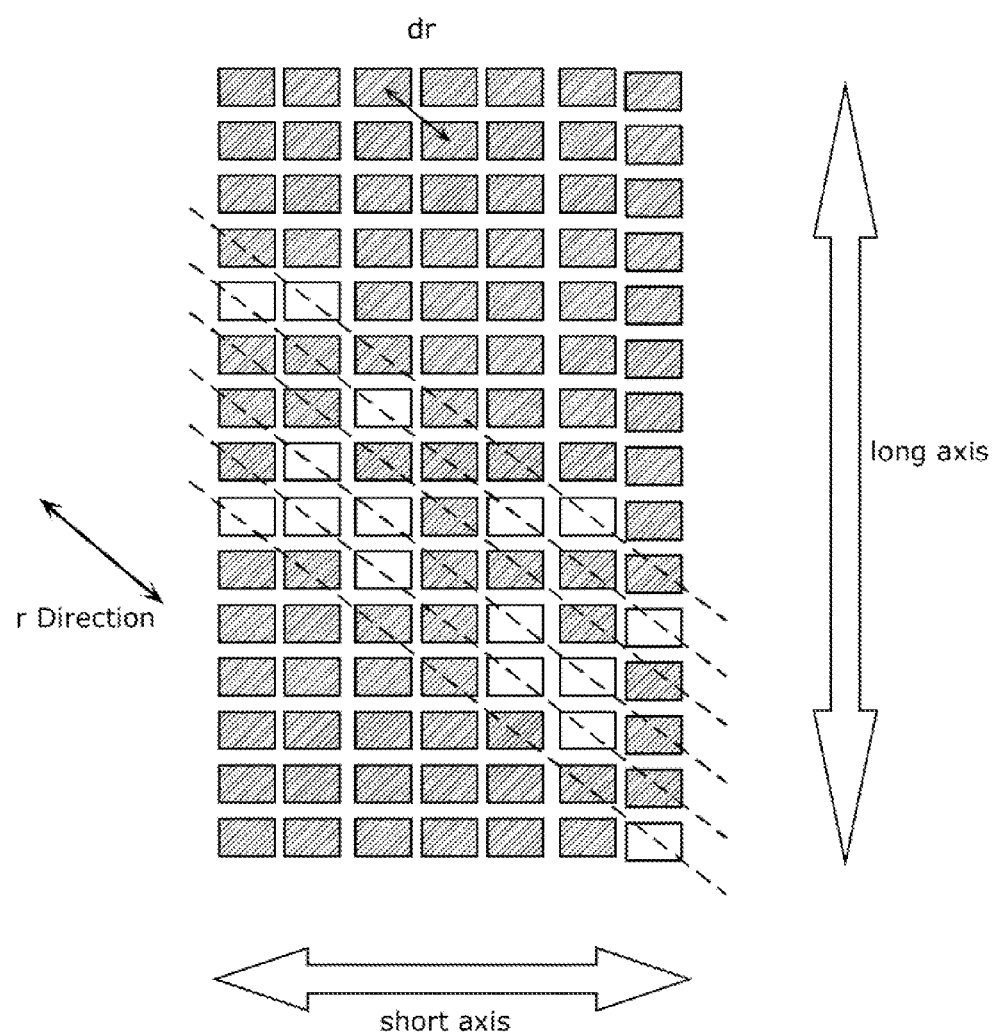
FIG. 14 is a diagram showing an example of a beamforming method according to a fourth embodiment of the present invention.

FIG. 14 is a diagram showing processing based on an array in an oblique direction.

For example, as shown in FIG. 14, it is possible to select, as used receiving elements (signals) which are a part of the receiving elements, respective receiving elements (signals) to be used in seed beam forming from among a plurality of ultrasonic receiving elements arrayed in a direction (hereinafter, referred to as an "oblique direction") that is not parallel to any of the short axis and the long axis of the two-dimensional probe.

In FIG. 14, the receiving elements to be used in the seed beam forming are shown as hatched.

Figure 15:
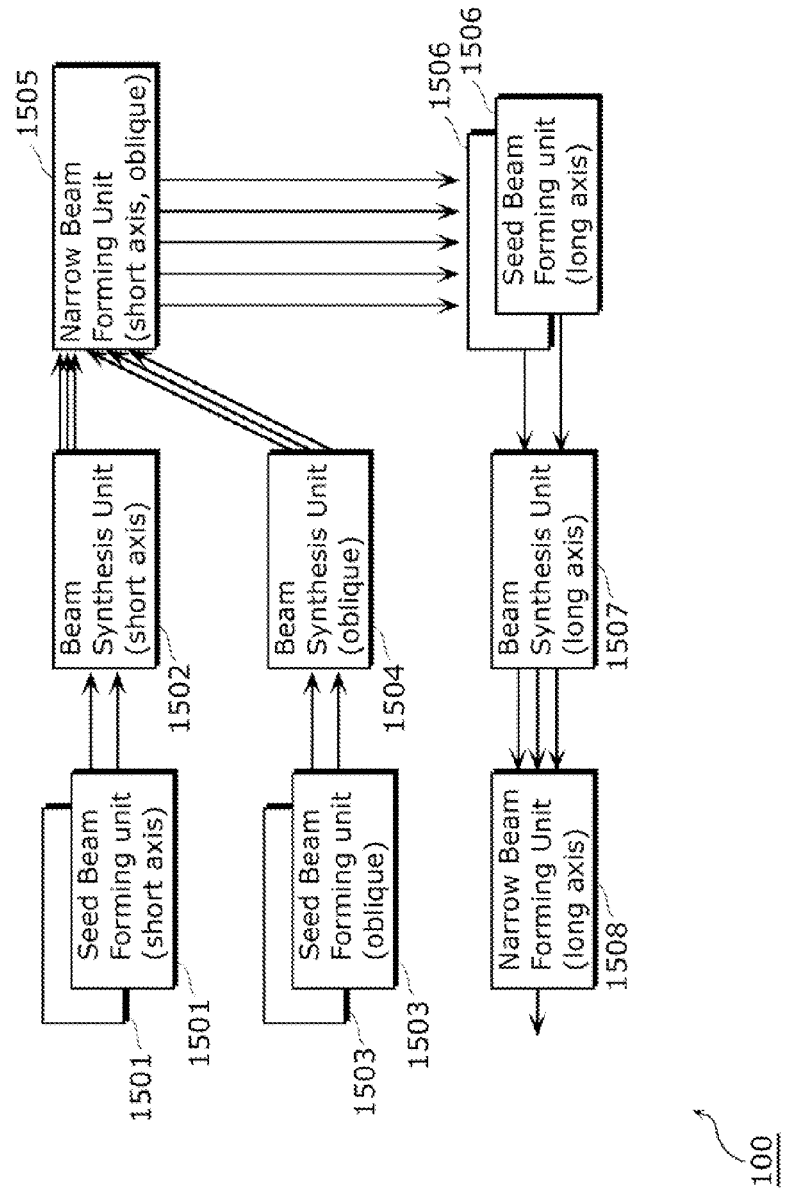
FIG. 15 is a diagram showing an example of the beamforming method according to the third embodiment of the present invention.

FIG. 15 is a block diagram (one example) of the beamformer (see FIG. 14 as described above) of the plurality of receiving elements which are two-dimensionally arrayed.

In comparison to the case where the plurality of receiving elements are one-dimensionally arrayed in Embodiment 1, the plurality of receiving elements are two-dimensionally arrayed so that a flexibility of combining the receiving elements is increased. As a result, variations of received beams can be increased. Accordingly, in comparison to the case where the plurality of receiving elements are one-dimensionally arrayed, it is possible to more adequately reduce noise incorporated from regions except the target region, and to further increase resolution by more appropriate narrow beam forming. It is expected to achieve more appropriate operations for these two effects.

The apparatus according to the present embodiment includes a receiving unit (not shown) including the plurality of receiving elements which are two-dimensionally arrayed.

The apparatus includes a plurality of seed beam forming units (short axis) 1501, a beam synthesis unit (short axis) 1502, a plurality of seed beam forming units (oblique) 1503, a beam synthesis unit (oblique) 1504, a narrow beam forming unit (short axis, oblique) 1505, a plurality of seed beam forming units (long axis) 1506, a beam synthesis unit (long axis) 1507, and a narrow beam forming unit (long axis) 1508.

Here, respective processes performed by the seed beam forming units, the beam synthesis unit, and the narrow beam forming unit are basically the same as the respective processes performed by the seed beam forming units, the beam synthesis unit, and the narrow beam forming unit according to Embodiment 1.

Therefore, the following aspect is characteristic. A direction of arraying receiving elements which receive signals to be processed by each of the functional blocks of the seed beam forming units, the beam synthesis unit, and the narrow beam forming unit is a direction (short-axis direction, oblique direction, long-axis direction) indicated within brackets in the functional block. The above-mentioned characteristics are that the processing of the functional block is performed by using a combination of a plurality of receiving elements arrayed in the direction.

Therefore, in the embodiment shown in FIG. 15, both of the beamformer using receiving elements in the short-axis direction and the beamformer using receiving elements in the oblique direction are performed. Then, a result of the beamformer is calculated for each element in each long-axis direction. Then, as beamformer for each element in each long-axis direction, processes of the seed beam forming unit (long axis) 1506, the beam synthesis unit (long axis) 1507, the narrow beam forming unit (long axis) 1508 at the following stage are performed. The above-mentioned characteristics are that a narrow beam is obtained by the above processes.

Figure 23:
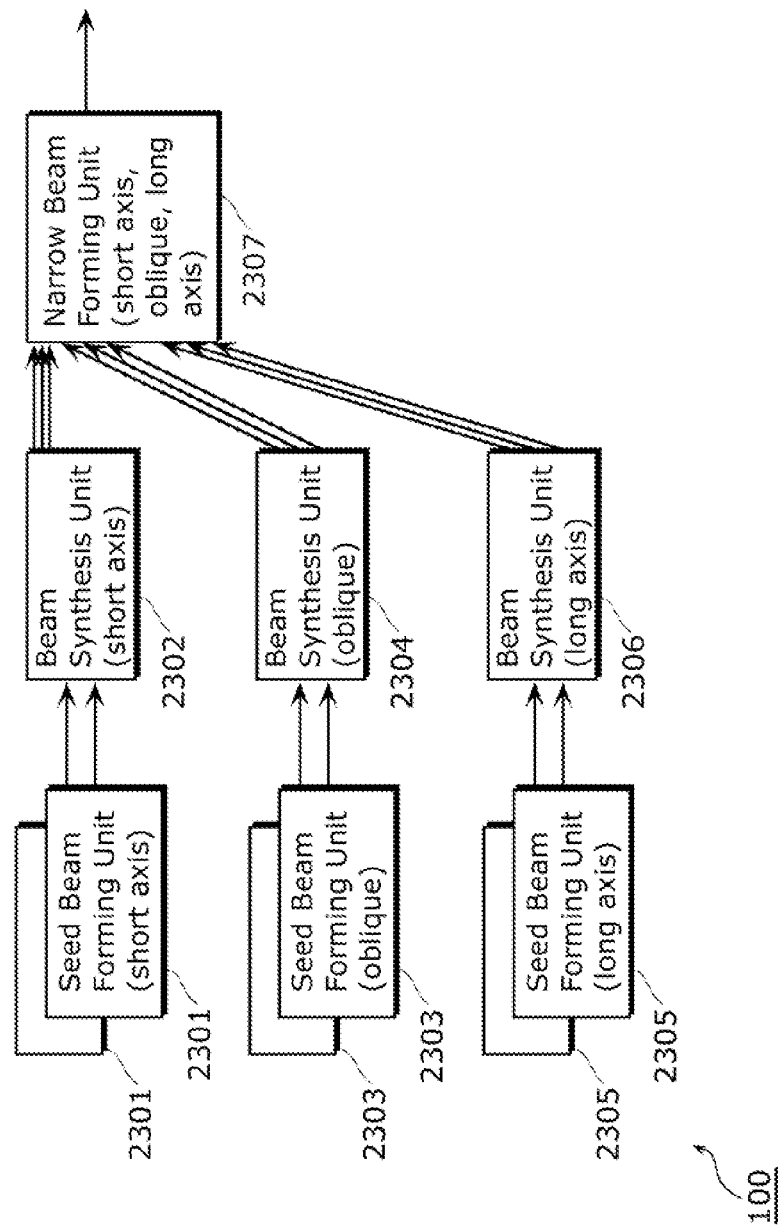
FIG. 23 is a block diagram showing beamformers in receiving element arranged two-dimensionally.
Figure 24:
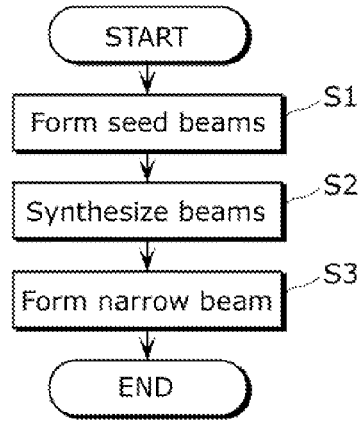
FIG. 24 is a flowchart of the technique according to the present invention.

FIG. 23 is a diagram showing an example of a block diagram of the beamformer for the two-dimensionally arrayed receiving elements.

In comparison to the case where the plurality of receiving elements are one-dimensionally arrayed in Embodiment 1, the plurality of receiving elements are two-dimensionally arrayed so that a flexibility of combining the receiving elements is increased. Therefore, variations of the received beams can be increased. Accordingly, in comparison to the case where the plurality of receiving elements are one-dimensionally arrayed, it is possible to more adequately reduce noise incorporated from regions except the target region, and to further increase resolution by more appropriate narrow beam forming. It is expected to achieve more appropriate operations for these two effects.

The apparatus according to the present embodiment includes a receiving unit (not shown) including the plurality of receiving elements which are two-dimensionally arrayed.

The apparatus includes a plurality of seed beam forming units (short axis) 2301, a beam synthesis unit (short axis) 2302, a plurality of seed beam forming units (oblique) 2303, a beam synthesis unit (oblique) 2304, a plurality of seed beam forming units (long axis) in 2305, a beam synthesis unit (long axis) 2306, and a narrow beam forming unit (short axis, oblique, long axis) 2307.

Then, in the case of this block structure, by using receiving elements arrayed in a direction indicated within brackets (long-axis direction, for example), the functional block with the indication performs the seed beam forming and the beam synthesis forming in the same manner as described in Embodiment 1. Then, by using a plurality of synthesized beams, the narrow beam forming unit 2307 forms a narrow beam. In this case, it is possible not to perform the beam forming by using the receiving elements arrayed in the oblique direction in view of a size of the arithmetic operation amount.

Embodiment 4

Figure 16:
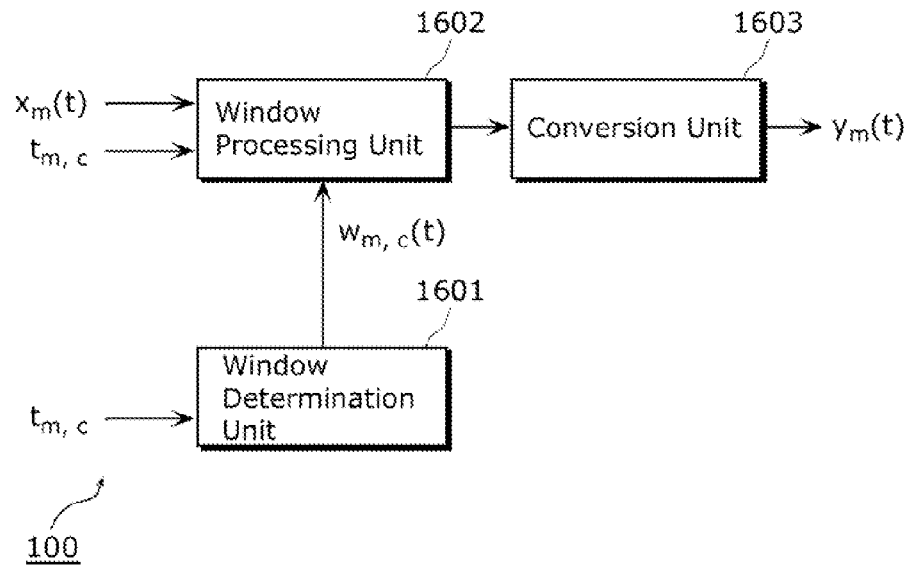
FIG. 16 is a block diagram showing a preparation unit according to a fourth embodiment of the present invention.

FIG. 16 is a block diagram showing the preparation unit 302 of the beamformer unit which has been described in Embodiment 1.

In FIG. 16, a window determination unit 1601, a window processing unit 1602, and a conversion unit 1603 form the preparation unit 302.

Prior to description of processing performed by the preparation unit 302 with reference to FIG. 16, the description is given with reference to FIG. 17.

Figure 17A:
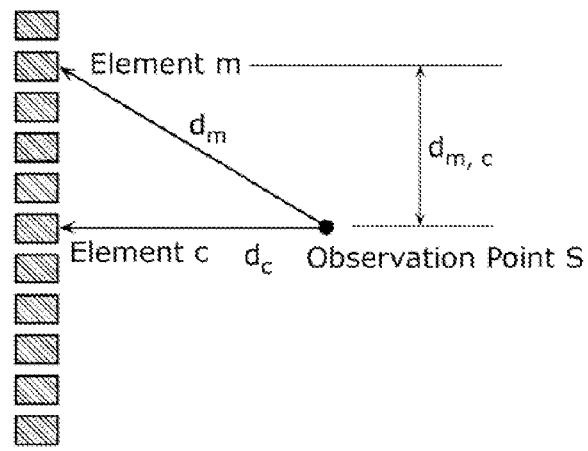
FIG. 17A is a diagram showing a positional relationship between receiving elements and an observation point.

FIG. 17A is a diagram showing a positional relationship between the plurality of receiving elements and an observation point S in the ultrasonic diagnostic apparatus. FIG. 17A shows the case where a receiving element the closest to the observation point S is a receiving element c.

A receiving element m is different from the receiving element c. A distance between the observation point S and the receiving element c is expressed as a distance $d_c$, while a distance between the observation point S and the receiving element m is expressed as a distance $d_m$. A distance between the receiving element m and the receiving element c is expressed as a distance $d_{m,r}$. For the sake of simplicity of the explanation, it is assumed that the plurality of receiving elements are arranged along a straight line, and that there is the center of the element c at a cross-point between the straight line of the receiving elements (the vertical straight line in FIG. 17A) and a line from the observation point perpendicular to the straight line. It should be noted that the present invention is not limited to the above structure.

Ultrasonic signals transmitted towards the observation point S are reflected on the observation point S and received by the respective receiving elements as received waves.

Figure 17B:
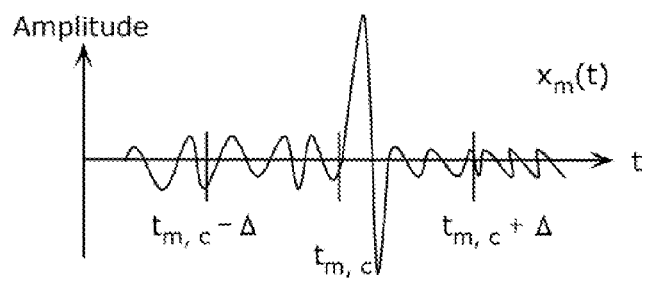
FIG. 17B is a graph plotting an example of a received waveform.

FIG. 17B is a diagram showing the received signals.

If pulse signals are used as transmission signals, the received signals as seen in FIG. 17B are observed as the above received signals.

In the graph of FIG. 17B, a horizontal axis indicates a time, and a vertical axis indicates an amplitude of the ultrasonic received signals received by the receiving element m.

Since the element m and the element c have different spatial distances from the observation point S, the received signals received by the elements generally arrive more later as the spatial distance is longer due to reflection on the observation point S.

Therefore, a delay occurs in proportional to a difference $(d_m-d_c)$ between (a) the distance $d_m$ between the observation point S and the receiving element m and (b) the distance $d_c$ between the observation point S and the receiving element c.

However, such a delay occurs when it is considered that a sonic speed of ultrasound propagated between the observation point S and the respective receiving elements is eventually the same between two respective paths of the ultrasound.

If there are different mediums on the paths from the observation point S to the respective receiving elements, it is not possible to expect the above-mentioned delay proportional to the difference between the distance $d_m$ and the distance $d_c$.

It is said that a sonic speed of ultrasound through a body is about 1440 m/s through fat as a medium and about 1570 m/s through blood, and that there is a difference of about ±5% around 1500 m/s in a sonic speed.

Furthermore, a sonic speed varies depending on environmental conditions such as a temperature.

Therefore, when the receiving element m in FIG. 17A receives reflection waves from the observation point S, it would be estimated that an arrival time in the case of a sonic speed of 1500 m/s is $d_m/1500$ seconds later. However, in reality, the arrival time may be delayed from the $d_m/1500$ seconds due to the above-described factors.

FIG. 17B is a diagram showing that there is a delay of $\pm\Delta$ time period for an arrival time in reality even if the arrival time is estimated as $t_{m,c}$.

Figure 17C:
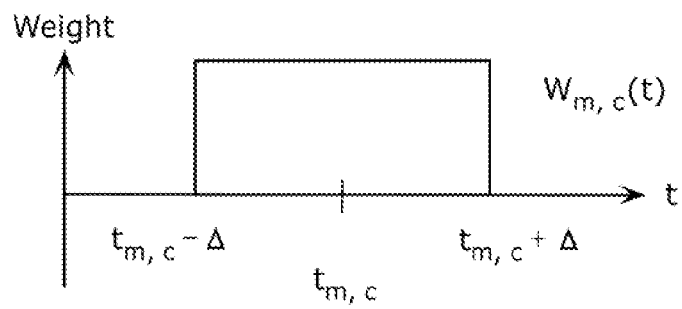
FIG. 17C is a graph plotting an example of a window function.

FIG. 17C is a diagram showing an example of a window in consideration of a delay width of the delay.

In FIG. 17C, a horizontal axis indicates a time, and a vertical axis indicates a window coefficient (corresponding to a weighting coefficient).

It is assumed that the window coefficient is determined based on (a) a relational relationship between the receiving element m and the receiving element c such as the distance $d_{m,c}$ between the two receiving elements, (b) the distance $d_m$ between the observation point S and the receiving element m, and the like.

This is for the following reason. If a spatial distance between the observation point S and the receiving element m is long and there is the above-described difference of ±5% in the sonic speed, it is considered that an arrival time is delayed by about 5% with respect to the distance $d_m$. Therefore, in comparison to the spatial distance $d_c$ between the observation point S and the receiving element c, $d_c<d_m$ which means $d_m$ is greater than $d_c$. Therefore, it is supposed that the arrival time delay for the receiving element m is generally longer than the arrival time delay for the receiving element c. This is the reason.

Next, the description is given with reference to FIG. 16.

FIG. 16 explains processing performed by the preparation unit 302 shown in FIG. 3.

The window determination unit 1601 makes determinations. More specifically, the window determination unit 1601 determine the positional relationship between the receiving element m and the receiving element c, namely, the distance $d_{m,c}$ between the two receiving elements, the distance $d_m$ between the observation point S and the receiving element m, and the distance d, between the observation point S and the receiving element c. In addition, the window determination unit 1601 also determine an estimated sonic speed of ultrasound, an estimated $t_m$ which is calculated from a sampling frequency or the like, and a time delay value $\Delta$ of $t_{m,c}$ which is set in view of a sonic speed delay and the like. The window determination unit 1601 determine them to determine a window $w_{m,c}(t)$ to be multiplied by the digital received signals.

When a delay of the sonic speed is estimated as about 5%, the time delay value $\Delta$ may be set to a value of 5% for $t_{m,c}$ or may be a value of about 0.5% as an actual implement value.

For example, in the case where $d_c=2$ cm, $d_{m,c}=0.5$ cm, an estimated sonic speed is 1500 m/s, and a sampling frequency is 40 MHz, $d_m=2.06$ cm.

When reflection from the observation point S is received at the estimated sonic speed, the reflection waves arrive with 549 samples by the above-described sampling frequency, and its 5% delay becomes 27-sample delay. In the case of about 0.5% implementation, 27/(5/0.5)=2.7, which means 2 or 3 samples. In the case of the above-described rectangular window in FIG. 17C, $w_{m,c}(t)$ with 3 samples of this Δ is a window determined by the window determination unit 1601.

The window processing unit 1602 multiplies a digital signal $x_m(t)$ by the window $w_{m,c}(t)$.

[Math. 9]

$$p(t) = w_{m,c}(t) \cdot x_m(t).$$ (Equation 9)

On the p(t) calculated according to the above-presented Equation 9, the conversion unit 1603 performs conversion to calculate an absolute value as determined by the following Equation 10, thereby calculating an output signal $y_m(t)$ of the preparation unit 302.

[Math. 10]

$$y_m(t) = |p(t)|$$ (Equation 10)

The conversion unit 1603 may calculate the output signal $y_m(t)$ by squaring p(t) or raising an absolute value (|p(t)|) to the α-th power in the arithmetic operation as determined by the following Equation 11 or 12. Here, α is a value on implementation, and an example of α is a value suitable for the present embodiment.

[Math. 11]

$$y_m(t) = (p(t))^2$$ (Equation 11)

[Math. 12]

$$y_m(t) = [|p(t)|]^\alpha$$ (Equation 12)

Thus, by using $y_m(t)$ calculated by the preparation unit 302, the delay addition unit 303 performs addition operation on the signals which have been generated by conversion and the like on the received signals received by the receiving element m and the like, so as to observe reflection on the observation point S.

[Math. 13]

$$bf_s = \sum_m \sum_t y_m(t)$$ (Equation 13)

As determined by the above Equation 13, $y_m(t)$ with varying t is summed, and the resulting sum is further summed by varying the value m of each receiving element m, so that the eventual sum is an output of the receiving method for the observation point S.

As described above, the position of the observation point S is varied, so that calculation is performed for each of the various positions in the designated region. With the above, in the ultrasonic diagnostic apparatus according to the present invention, drawing is executed after performing processing, such as processing of reducing samples and processing of calculating an intensity using an exponent function, based on the value generated by the above-presented Equation 13.

Figure 18:
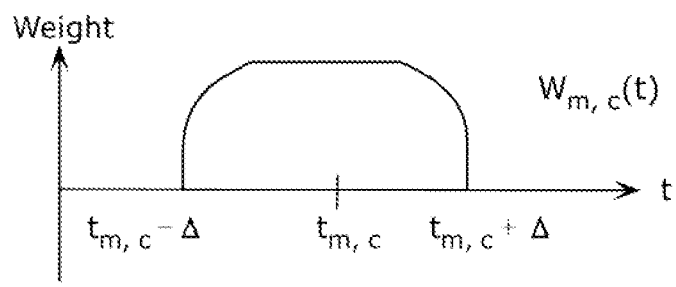
FIG. 18 is a graph plotting an example of a window function shape (in the case of a symmetrical shape).
Figure 19:
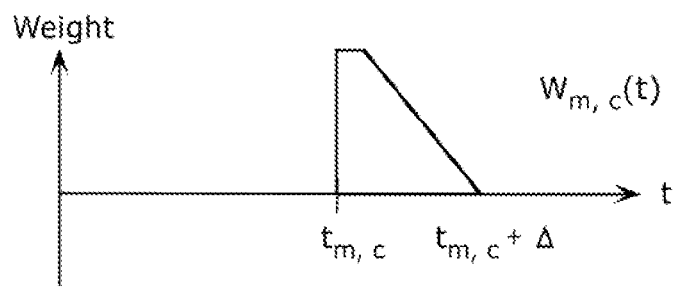
FIG. 19 is a graph plotting an example of a window function shape (in the case of only one side).
Figure 20:
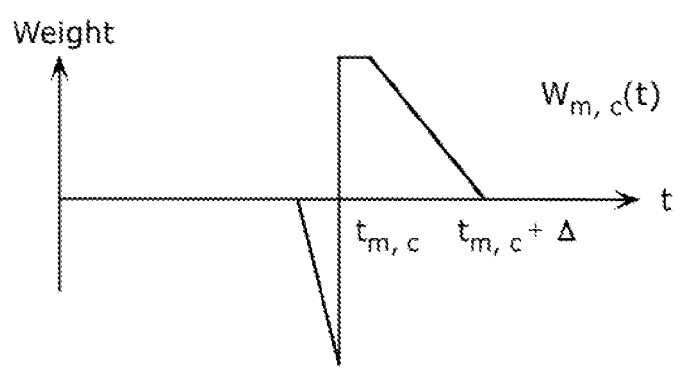
FIG. 20 is a graph plotting an example of a window function shape (in the case of asymmetry).

Each of FIGS. 18, 19, and 20 is a diagram showing a window shape.

It has been described with reference to FIG. 17C that the window function is the rectangular window as an example.

On the other hand, in FIG. 18 shows a plurality of window shapes which are symmetrical with respect to $t_{m,c}$.

FIG. 19 shows a window shape having a width of a maximum +Δ in a plus direction.

FIG. 20 shows an asymmetry window shape.

In the case of the symmetry shape in FIG. 19, it is expected to from seed beams having robustness convolved with frequency characteristics of the window shape.

In the case of FIG. 19, in the value calculation for each $t_{m,c}$, the influence in a minus direction is not considered. Therefore, it is expected that a delay of a sonic speed does not influence for a long period (a period with a time width both in the plus direction and the minus direction with respect to $t_{m,c}$ as the center).

Like the case of FIG. 18, the above also has robustness convolved with frequency characteristics of the window shape.

In the case of FIG. 19, with respect to $t_{m,c}$ as the center, influence in the minus direction is more subtracted, and a value in the plus direction is added. Thereby, in addition to the robustness, effects of edge emphasis can be expected as effects to the eventual image quality.

In each of Embodiments 1 to 3, it is considered that the preparation (the preparation unit 302) in the beam forming is performed as described above. In accordance with such preparation, the receiving method using the seed beam forming units 202, the beam synthesis unit 203, and the narrow beam forming unit 204 in FIG. 2, namely, the beamforming, is as follows. By performing as described above, in comparison to the conventional example explained in Embodiment 1, it is possible not only to increase resolution and further suppress noise, but also to provide robustness for influence such as sonic speed delay occurred in applying the present invention to a body.

It is also possible that the user can select a window function shape and a window length. In other words, the ultrasonic diagnostic apparatus has a window function conversion structure. It is further possible that a window function conversion button and a window length conversion button are displayed with a displayed image, or that a window function change tab and a window length change tab are provided to the apparatus.

It should be noted that even a combination of Embodiment 4 with the conventional ultrasonic diagnostic apparatus and beamforming method can offer better effects.

Embodiment 5

As described above, in summary, it is possible to increase resolution and image quality of the ultrasonic diagnostic apparatus. More specifically, the beamforming method is used, and the beamforming method is characterized by including: a seed beam forming step of forming various kinds of seed beams from various different combinations of receiving elements using echo signals, by using echo signals obtained from a part of the receiving element group; a beam synthesis step of selecting plural kinds of seed beams to synthesize them to form at least (a) a main beam having a high signal intensity for the target region and (b) sub beams having a signal intensity for the target region which is lower than that of the main beam; and a narrow beam forming step of multiplying the sub beams by respective coefficients and subtracting the resulting sub beams from the main beam so as to synthesize an echo signal for the target region.

It should be noted that a value (intensity) of the main signal 92 (FIG. 25) and a value (intensity) of the sub signal 91 in each of a main lobe and a side lobe may be as follows.

The sub signal 91 may be the following sub signal.

The sub signal has a value of a main lobe which is a signal equal (substantially equal) to 0.

The sub signal has a value of a side lobe which is a signal equal (substantially equal) to a value of a side lobe of the main signal 92.

It is confirmed that, if the sub signal 91 is such a sub signal in the present invention, the generated signal 105a (FIG. 25) which is generated by subtracting the sub signal 91 is (or is relatively often) the above-described appropriate second subtracted signal.

It is therefore possible that the value of the main lobe of the generated sub signal 91 is equal (substantially equal) to 0 and the value of the side lobe of the generated sub signal 91 is substantially equal to the value of the side lobe of the main signal 92.

Although the present invention has been described using the above embodiments, the present invention is, of course, not limited to the above embodiments and includes the following variations.

For example, it is also possible that the present invention is a computer system including a microprocessor and a memory, the memory holds the above-described computer program, and the microprocessor is executed by the computer program. For example, it is possible that the computer system includes a computer program of a diagnosis method of the ultrasonic diagnostic apparatus according to the present invention, and operates (or instructs respective connected parts to operate) in accordance with the program.

It should be noted in the present invention that all or a part of the above-described ultrasonic diagnostic apparatus or all or a part of the beamforming unit may be implemented as a computer system that includes a microprocessor, a recording medium such as a Read Only Memory (ROM) and a Random Access Memory (RAM), hard disk unit, and the like. The RAM or the hard disk unit holds a computer program for executing the same processing as performed by each of the above-described apparatuses. The microprocessor operates in accordance with the computer program to allow each apparatus to perform the functions.

It should be noted that a part or all of the structural elements included in each of the above-described apparatuses may be implemented into a single Large Scale Integration (LSI). The system LSI is a super multi-function LSI that is a single chip into which a plurality of structural elements are integrated. More specifically, the system LSI is a computer system including a microprocessor, a ROM, a RAM, and the like. The RAM holds a computer program for executing the same processing as performed by each of the above-described apparatuses. The microprocessor is executed by the computer program to cause the system LSI to perform its functions. For example, it is also possible that the beamforming method according to the present invention is stored as a program of the LSI so that a predetermined program (beamforming method) is executed.

It is further possible that the diagnosis method of the above-described ultrasonic diagnostic apparatus or a program or signal for executing the beamforming method is recorded on a recorded medium and transferred so that the program is executed by an different independent computer system.

Finally, needless to say, the above-described embodiments can be combined to each other.

INDUSTRIAL APPLICABILITY

The receiving method of the ultrasonic diagnostic apparatus according to the present invention includes a plurality of seed beam forming units, the beam synthesis unit, and the narrow beam forming unit, and is useful to improve performance and, in particular, image quality of conventional ultrasonic diagnostic apparatuses. The present invention can be applied not only to ultrasonic but also to sensors using a plurality of array elements and the like.

REFERENCE SIGNS LIST 101 probe unit
102 T/R switch unit
103 pulsar unit
104 AFE unit
105 beamformer unit
106 imaging unit
107 display unit
108 operation unit
201 receiving unit
202 seed beam forming unit
203 beam synthesis unit
204 narrow beam forming Unit
205 receiving element
300 receiving unit
301 seed beam switch unit
302 preparation unit
303 delay addition processing unit
701 weighted-beam addition unit
702 weighted-beam multiplication unit
703 beam expectation value operation unit
801 temporary beam synthesis unit
802 main beam synthesis sub-unit
803 sub beam synthesis sub-unit
901 weighted-beam addition unit
902 main beam preparation unit
903 weighted-beam subtraction unit
1001 receiving unit
1002 receiving element
1101 probe unit
1102 beamformer unit
1103 seed beam forming unit
1104 beam synthesis unit
1105 narrow beam forming Unit
1106 image generation unit
1107 data storage unit (cine memory)
1108 image display unit
1109 control unit
1301, 1304 seed beam forming unit
1302, 1305 beam synthesis unit
1303, 1306 narrow beam forming Unit
1501, 1503, 1506 seed beam forming unit
1502, 1504, 1507 beam synthesis unit
1505, 1508 narrow beam forming unit
1601 window determination unit
1602 window processing unit
1603 conversion unit
2203 beam synthesis/narrow beam forming unit
2301, 2303, 2305 seed beam forming unit
2302, 2304, 2306 beam synthesis unit
2307 narrow beam forming unit
S1, S2, S3 step

The invention claimed is:

1. A beamforming method of processing echo signals of a target region, the echo signals being obtained from a probe including a plurality of receiving elements arrayed on a predetermined line, the beamforming method comprising:
   forming seed beams from echo signals received by at least two receiving elements from among the plurality of receiving elements;
   forming a main beam and a sub beam by using at least one of the seed beams; and forming a narrow beam for the target region, by multiplying the sub beam by a predetermined coefficient and subtracting the multiplied sub beam from the main beam, wherein a beam width of a main lobe of the narrow beam is shorter than a beam width of a main lobe of the main beam, and wherein a signal intensity for the target region regarding the main beam is higher than a signal intensity for the target region regarding the sub beam.

2. The beamforming method according to claim 1, wherein each of the seed beams is formed from echo signals obtained by changing a combination of the at least two receiving elements.

3. The beamforming method according to claim 1, wherein the forming of the seed beams does not use echo signals received by at least one of receiving elements located between two receiving elements at both ends of the predetermined line.

4. The beamforming method according to claim 1, wherein a beam width of a main lobe of at least one of the seed beams is shorter than a beam width of a main lobe of a beam which is formed from the echo signals received by all of the plurality of receiving elements.

5. The beamforming method according to claim 1, wherein the forming of the main beam and the sub beam uses at least two kinds of arithmetic operations to form the main beam and the sub beam.

6. The beamforming method according to claim 1, wherein, in the forming of the seed beams, at least one of the seed beams is formed from the echo signals received by all of the plurality of receiving elements.

7. The beamforming method according to claim 1, wherein receiving elements which are included in the plurality of receiving elements and receive echo signals to be used are symmetric with respect to a center point of a region between two receiving elements at both ends of the receiving elements which receive the echo signals to be used.

8. The beamforming method according to claim 1, wherein a number of at least one of the plurality of receiving elements which receives echo signals not to be used and is located between two receiving elements receiving echo signals to be used is constant.

9. The beamforming method according to claim 1, wherein, in the forming of the seed beams, a seed beam switch for switching whether or not to use echo signals received by each of the plurality of receiving elements is turned OFF to select one or more receiving elements as not to contribute in the forming of the seed beams, so that there is periodically one or more consecutive receiving elements not to contribute in the forming of the seed beams.

10. The beamforming method according to claim 1,
wherein in the forming of the main beam and the sub beam, a plurality of sub beams are formed, and
wherein a number of the main beam and the sub beams which are formed in the forming of the main beam and the sub beam is greater than a number of the seed beams formed in the forming of the seed beams.

11. The beamforming method according to claim 1,
wherein in the forming of the main beam and the sub beam, a plurality of sub beams are formed, and
wherein the narrow beam formed in the forming of the narrow beam is a beam for the target region and formed by subtracting, from a value of the main beam, a sum of values each of which is calculated by multiplying a value of a corresponding one of the sub beams by a suppression coefficient.

12. The beamforming method according to claim 1, wherein the forming of the seed beams includes:

multiplying the echo signals received by the at least two receiving elements by a window function with a predetermined time width and a predetermined intensity; and
forming the seed beams from the multiplied echo signals.

13. The beamforming method according to claim 1, wherein:
the target region comprises a first target region and a second target region,
a distance from a body surface to the second target region is longer than a distance from the body surface to the first target region, and
a number of openings of receiving elements selected when the seed beams are formed from echo signals received from the second target region is greater than a number of openings of receiving elements selected when the seed beams are formed from echo signals received from the first target region.

14. An ultrasonic diagnostic apparatus which processes echo signals of a target region, the echo signals being obtained from a probe including a plurality of receiving elements arrayed on a predetermined line, the ultrasonic diagnostic apparatus comprising:
a seed beam forming unit configured to form seed beams from echo signals received by at least two receiving elements from among the plurality of receiving elements;
a beam synthesis unit configured to form a main beam and a sub beam by using at least one of the seed beams;
a narrow beam forming unit configured to form a narrow beam for the target region, by multiplying the sub beam by a predetermined coefficient and subtracting the multiplied sub beam from the main beam, wherein a beam width of a main lobe of the narrow beam is shorter than a beam width of a main lobe of the main beam; and
an imaging unit configured to generate an image of the narrow beam formed by the narrow beam forming unit,
wherein a signal intensity for the target region regarding the main beam is higher than a signal intensity for the target region regarding the sub beam.

15. The ultrasonic diagnostic apparatus according to claim 14,
wherein the beam synthesis unit is configured to form a plurality of sub beams, and
wherein a number of the sub beams formed when a frame rate of the image generated by the imaging unit is a first frame rate is lower than a number of the sub beams formed when the frame rate is a second frame rate that is higher than the first frame rate.

16. A non-transitory computer-readable recording medium having a computer program recorded thereon for causing a computer to processes echo signals of a target region, the echo signals being obtained from a probe including a plurality of receiving elements arrayed on a predetermined line, and the computer program causing the computer to execute:
forming seed beams from echo signals received by at least two receiving elements from among the plurality of receiving elements;
forming a main beam and a sub beam by using at least one of the seed beams; and
forming a narrow beam for the target region, by multiplying the sub beam by a predetermined coefficient and subtracting the multiplied sub beam from the main beam, wherein a beam width of a main lobe of the narrow beam is shorter than a beam width of a main lobe of the main beam, and wherein a signal intensity for the target region regarding the main beam is higher than a signal intensity for the target region regarding the sub beam.

17. An integrated circuit which processes echo signals of a target region, the echo signals being obtained from a probe including a plurality of receiving elements arrayed on a predetermined line, the integrated circuit comprising:
- a seed beam forming unit configured to form seed beams from echo signals received by at least two receiving elements from among the plurality of receiving elements;
- a beam synthesis unit configured to form a main beam and a sub beam by using at least one of the seed beams; and
- a narrow beam forming unit configured to form a narrow beam for the target region, by multiplying the sub beam by a predetermined coefficient and subtracting the multiplied sub beam from the main beam, wherein a beam width of a main lobe of the narrow beam is shorter than a beam width of a main lobe of the main beam, and
wherein a signal intensity for the target region regarding the main beam is higher than a signal intensity for the target region regarding the sub beam.

18. The beamforming method of claim 1, wherein in the forming of the main beam and the sub beam, the main beam or the sub beam is formed by performing addition, multiplication, subtraction, or an expectation value operation on the seed beams, such that the signal intensity for the target region regarding the main beam is higher than the signal intensity for the target region regarding the sub beam.

19. The beamforming method according to claim 1, wherein in the forming of the narrow beam, a weighting coefficient is determined in accordance with change of a directivity of the narrow beam that is formed by changing the weighting coefficient.

20. The beamforming method according to claim 1,
- wherein in the forming of the main beam and the sub beam, a plurality of sub beams are formed, and
- in the forming of the narrow beam, the narrow beam is formed by multiplying the sub beams by respective predetermined coefficients and subtracting the multiplied sub beams from the main beam.

* * * * *